(12) United States Patent
Cragg et al.

(10) Patent No.: US 6,315,753 B1
(45) Date of Patent: Nov. 13, 2001

(54) SYSTEM AND METHOD FOR FACILITATING HEMOSTASIS OF BLOOD VESSEL PUNCTURES WITH ABSORBABLE SPONGE

(75) Inventors: Andrew M. Cragg, Edina, MN (US); Rodney Brenneman, San Juan Capistrano, CA (US); Mark Ashby, Laguna Niguel, CA (US); Eduardo Chi Sing, Dana Point, CA (US)

(73) Assignee: Sub-Q, Inc., San Clemente, CA (US)

(*) Notice: Subject to any disclaimer, the term of this patent is extended or adjusted under 35 U.S.C. 154(b) by 0 days.

(21) Appl. No.: 09/263,603

(22) Filed: Mar. 5, 1999

Related U.S. Application Data

(63) Continuation-in-part of application No. 09/071,284, filed on May 1, 1998, now Pat. No. 6,162,192.

(51) Int. Cl.[7] ...................................... A61F 13/20
(52) U.S. Cl. .............................................. 604/15
(58) Field of Search ........................... 604/11–18, 264, 604/57–60; 606/213

(56) References Cited

U.S. PATENT DOCUMENTS

| | | |
|---|---|---|
| 581,235 | 4/1897 | Kenyon . |
| 1,578,517 | 3/1926 | Hein . |
| 2,086,580 | 7/1937 | Shirley . |
| 2,465,357 | 3/1949 | Correll . |
| 2,492,458 | 12/1949 | Bering, Jr. . |

(List continued on next page.)

FOREIGN PATENT DOCUMENTS

| | | |
|---|---|---|
| 32826 A2 | 7/1981 | (EP) . |
| 476178 A1 | 3/1992 | (EP) . |
| 482350 A2 | 4/1992 | (EP) . |
| 1509023 | 4/1978 | (GB) . |
| 1 569 660 | 6/1980 | (GB) . |
| WO 96/08208 | 3/1996 | (WO) . |
| WO 98/06346 | 2/1998 | (WO) . |

OTHER PUBLICATIONS

Vincent P. Chuang, MD, et al. "Sheath Needle for Liver Biopsy in High–Risk Patients, " Radiology, 166:261–262 (1988).

Marc Zins, MD, et al., "US–guided Percutaneous Liver Biopsy with Plugging of the Needle Track: *A Prospective Study in 72 High–Risk Patients*," Radiology, 184(3):841–843 (1992).

Tony P. Smith, MD, et al., "*Percutaneous Transhepatic Liver Biopsy with Tract Embolization*," Radiology, 198:769–774 (1996).

S.A. Riley, et al., "Percutaneous Liver Biopsy With Plugging Of Needle Track: *A Safe Method For Use In Patients With Impaired Coagulation,* " The Lancet, pp. 436 (1984).

David J. Allison, MD, et al., "*Percutaneous Liver Biopsy and Track Embolization With Steel Coils*," Radiology, 169(1):261–263 (1988).

(List continued on next page.)

Primary Examiner—Dennis Ruhl
(74) Attorney, Agent, or Firm—Burns Doane Swecker & Mathis

(57) ABSTRACT

A method of superhydrating an absorbable sponge for delivery to a body to facilitate hemostasis includes the step of subjecting the absorbable sponge to a high pressure fluid to hydrate the absorbable sponge. According to one method, a dry piece of absorbable sponge is placed in a delivery device. The absorbable sponge is then subjected to a high pressure fluid by injecting fluid into the delivery device to rapidly and completely hydrate the absorbable sponge in the delivery device. The high pressure fluid used for rapidly and completely hydrating the absorbable sponge is delivered at a pressure of about 5 psi or greater. The hydrated absorbable sponge may be delivered to a puncture site in a blood vessel to facilitate hemostasis of the puncture site.

21 Claims, 14 Drawing Sheets

U.S. PATENT DOCUMENTS

| | | |
|---|---|---|
| 2,507,244 | 5/1950 | Correll . |
| 2,558,395 | 6/1951 | Studer . |
| 2,597,011 | 5/1952 | MacMasters et al. . |
| 2,680,422 | 6/1954 | Linzmayer . |
| 2,761,446 | 9/1956 | Reed . |
| 2,814,294 | 11/1957 | Figge . |
| 2,824,092 | 2/1958 | Thompson . |
| 2,899,362 | 8/1959 | Sieger, Jr. et al. . |
| 3,157,524 | 11/1964 | Artandi . |
| 4,000,741 | 1/1977 | Binard et al. . |
| 4,323,072 | 4/1982 | Rosenbluth et al. . |
| 4,340,066 | 7/1982 | Shah . |
| 4,390,018 | 6/1983 | Zulowski . |
| 4,515,637 | 5/1985 | Cioca . |
| 4,587,969 | 5/1986 | Gillis . |
| 4,588,395 | 5/1986 | Lemelson . |
| 4,619,261 | 10/1986 | Guerriero . |
| 4,619,913 | 10/1986 | Luck et al. . |
| 4,645,488 | 2/1987 | Matukas . |
| 4,744,364 | 5/1988 | Kensey . |
| 4,790,819 | 12/1988 | Li et al. . |
| 4,829,994 | 5/1989 | Kurth . |
| 4,850,960 | 7/1989 | Grayzel . |
| 4,852,568 | 8/1989 | Kensey . |
| 4,890,612 | 1/1990 | Kensey . |
| 4,900,303 | 2/1990 | Lemelson . |
| 4,929,246 | 5/1990 | Sinofsky . |
| 4,936,835 | 6/1990 | Haaga . |
| 4,950,234 | 8/1990 | Fujioka et al. . |
| 5,007,895 | 4/1991 | Burnett . |
| 5,021,059 | 6/1991 | Kensey et al. . |
| 5,053,046 | 10/1991 | Janese . |
| 5,061,274 | 10/1991 | Kensey . |
| 5,080,655 | 1/1992 | Haaga . |
| 5,108,421 | 4/1992 | Fowler . |
| 5,163,904 | 11/1992 | Lampropoulos et al. . |
| 5,167,624 | 12/1992 | Butler et al. . |
| 5,192,300 | 3/1993 | Fowler . |
| 5,192,301 | 3/1993 | Kamiya et al. . |
| 5,195,988 | 3/1993 | Haaga . |
| 5,220,926 | 6/1993 | Jones . |
| 5,221,259 | 6/1993 | Weldon et al. . |
| 5,275,616 | 1/1994 | Fowler . |
| 5,310,407 | 5/1994 | Casale . |
| 5,325,857 | 7/1994 | Nabai et al. . |
| 5,334,216 | 8/1994 | Vidal et al. . |
| 5,366,480 | 11/1994 | Corriveau et al. . |
| 5,383,896 | 1/1995 | Gershony et al. . |
| 5,383,899 | 1/1995 | Hammerslag . |
| 5,388,588 | 2/1995 | Nabai et al. . |
| 5,391,183 | 2/1995 | Janzen et al. . |
| 5,419,765 | 5/1995 | Weldon et al. . |
| 5,431,639 | 7/1995 | Shaw . |
| 5,437,631 | 8/1995 | Janzen . |
| 5,467,780 | 11/1995 | Nabai et al. . |
| 5,478,352 | 12/1995 | Fowler . |
| 5,479,936 | 1/1996 | Nabai et al. . |
| 5,486,195 | 1/1996 | Myers et al. . |
| 5,522,850 | 6/1996 | Yomtov et al. . |
| 5,526,822 | 6/1996 | Burbank et al. . |
| 5,529,577 | 6/1996 | Hammerslag . |
| 5,540,715 | 7/1996 | Katsaros et al. . |
| 5,545,178 | 8/1996 | Kensey et al. . |
| 5,558,853 | 9/1996 | Quay . |
| 5,591,204 | 1/1997 | Janzen et al. . |
| 5,591,205 | 1/1997 | Fowler . |
| 5,601,602 | 2/1997 | Fowler . |
| 5,645,566 | 7/1997 | Brenneman et al. . |
| 5,649,547 | 7/1997 | Ritchart et al. . |
| 5,653,730 | 8/1997 | Hammerslag . |
| 5,665,107 | 9/1997 | Hammerslag . |
| 5,681,279 | 10/1997 | Roper et al. . |
| 5,716,375 | 2/1998 | Fowler . |
| 5,725,498 | 3/1998 | Janzen et al. . |
| 5,741,223 | 4/1998 | Janzen et al. . |
| 5,769,086 | 6/1998 | Ritchart et al. . |
| 5,775,333 | 7/1998 | Burbank et al. . |
| 5,810,806 | 9/1998 | Ritchart et al. . |
| 5,830,130 | 11/1998 | Janzen et al. . |
| 5,902,310 | 5/1999 | Foerster et al. . |
| 6,007,563 | 12/1999 | Nash et al. . |
| 6,071,301 | * 6/2000 | Cragg et al. ................... 606/213 |

OTHER PUBLICATIONS

Sigmund Silber, MD, FACC, "Rapid Hemostasis of Arterial Puncture Sites With Collagen in Patients Undergoing Diagnostic and Interventional Cardiac Catheterization," Clinical Cardiology, 20:981–992 (1997).

Ferdinand Kiemeneij, MD, et al., "Improved Anticoagulation Management After Palmaz Schatz Coronary Stent Implantation by Sealing the Arterial Puncture Site with a Vascular Hemostasis Device," Catheterization and Cardiovascular Diagnosis, 30:317–322 (1993).

J.P.M. Foran, et al., "*Early Mobilisation After Percutaneous Cardiac Catheterisation Using Collagen Plug (VasoSeal) Haemostasis,* " Br. Heart J., 69:424–429 (1993).

Schrader, R., et al., "Collagen Application for Sealing of Arterial Puncture Sites in Comparison to Pressure Dressing: *A Randomized Trial*," Catheterization and Cardiovascular Diagnosis, 27(4):298–302 (1992).

J.S.R. Gibbs, "*Femoral Arterial Hemostasis Using a Collagen Plug After Coronary Artery Stent Implantation,*" Journal of Interventional Cardiology, 5(2):85–88 (1992).

W.G. Kussmaul III, et al., "Rapid Arterial Hemostasis and Decreased Access Site Complications After Cardiac Catheterization and Angioplasty: *Results of a Randomized Trial of a Novel Hemostatic Device*," J. Am. Coll. Cardiol., 25(7):1685–1692 (1995).

Timothy A. Sanborn, MD, et al., "Multicenter Randomized Trial Comparing a Percutaneous Collagen Hemostasis Device With Conventional Manual Compression After Diagnostic Angiography and Angioplasty," Journal of American College of Cardiology, 22(5):1273–1279 (1993).

Pharmacia & Upjohn Manufacturer Brochure, "*Gelfoam Sterile Sponge, Sterile Powder, and Sterile Film*," pp. 1–34 (May 1997).

Pharmacia & Upjohn Manufacturer Brochure, "*Gelfoam Sterile Powder*," 4 pages (Mar. 1996).

Pharmacia & Upjohn Manufacturer Specification, "*Gelfoam Sterile Sponge, Sterile Powder, and Sterile Film*," pp. 1–23 (Nov. 1996).

* cited by examiner

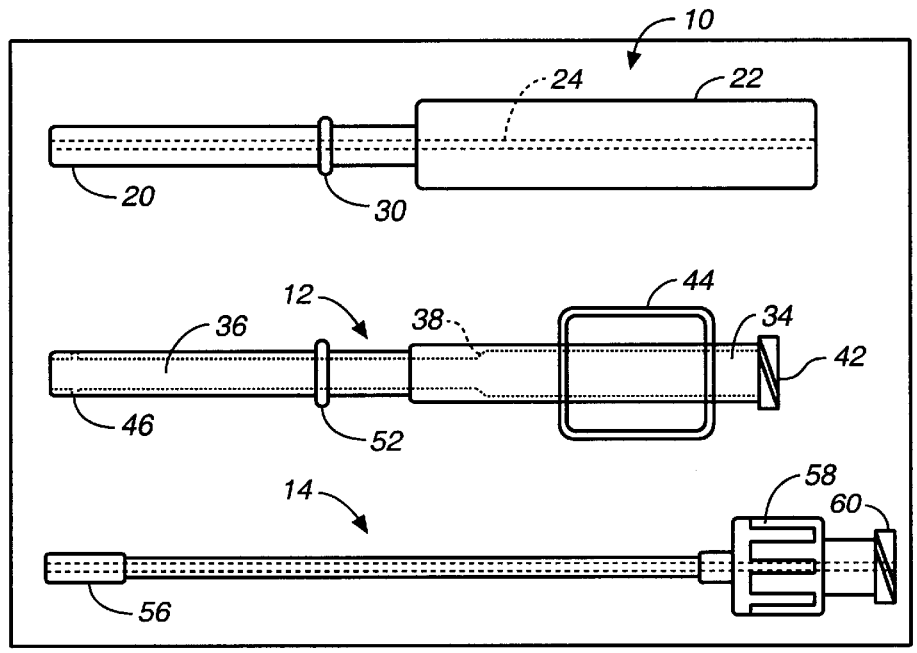
FIG._1
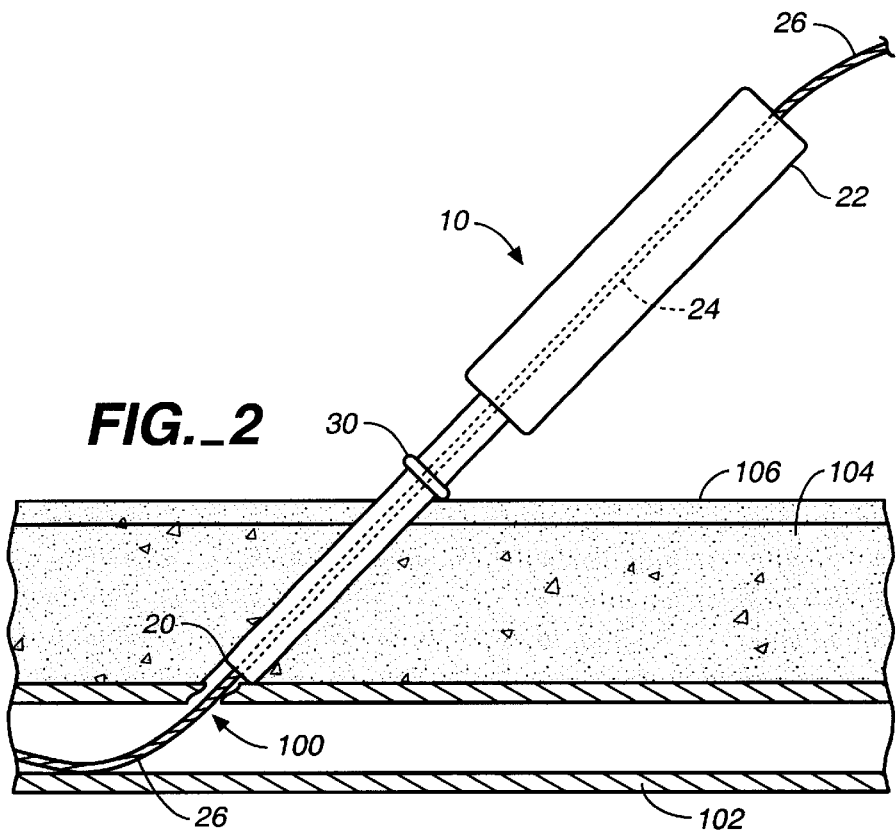
FIG._2

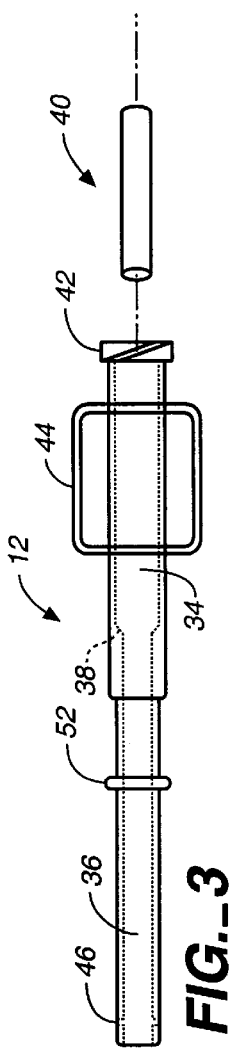
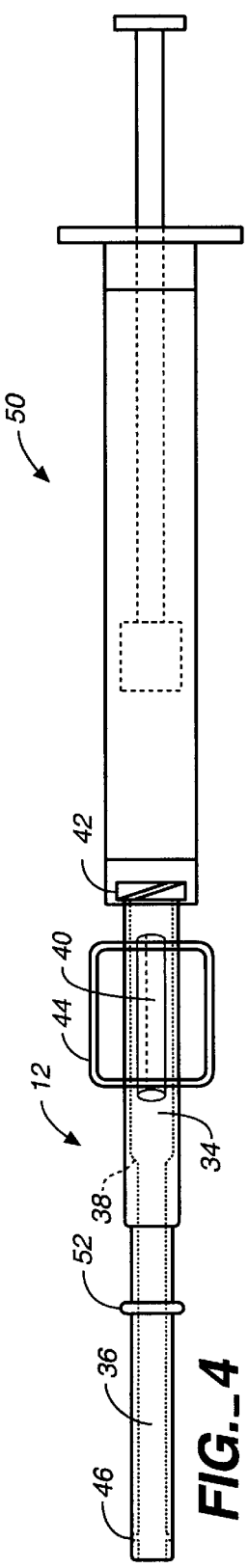
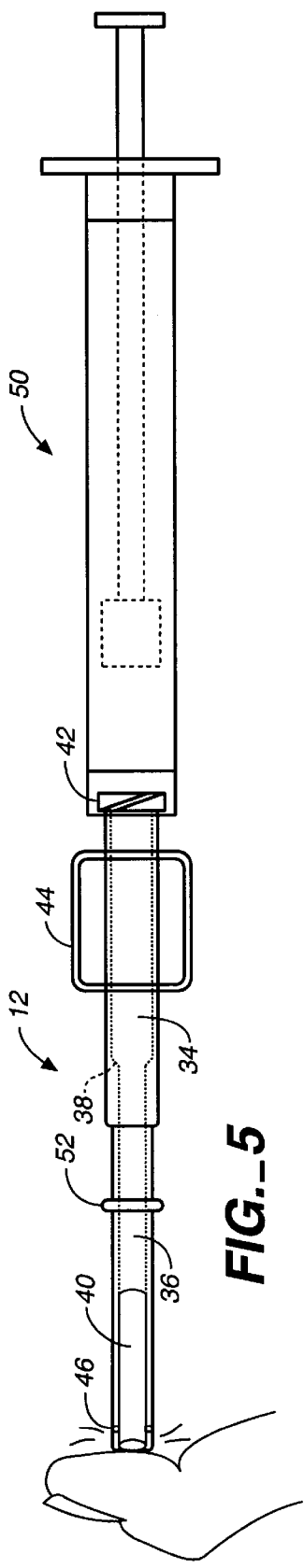

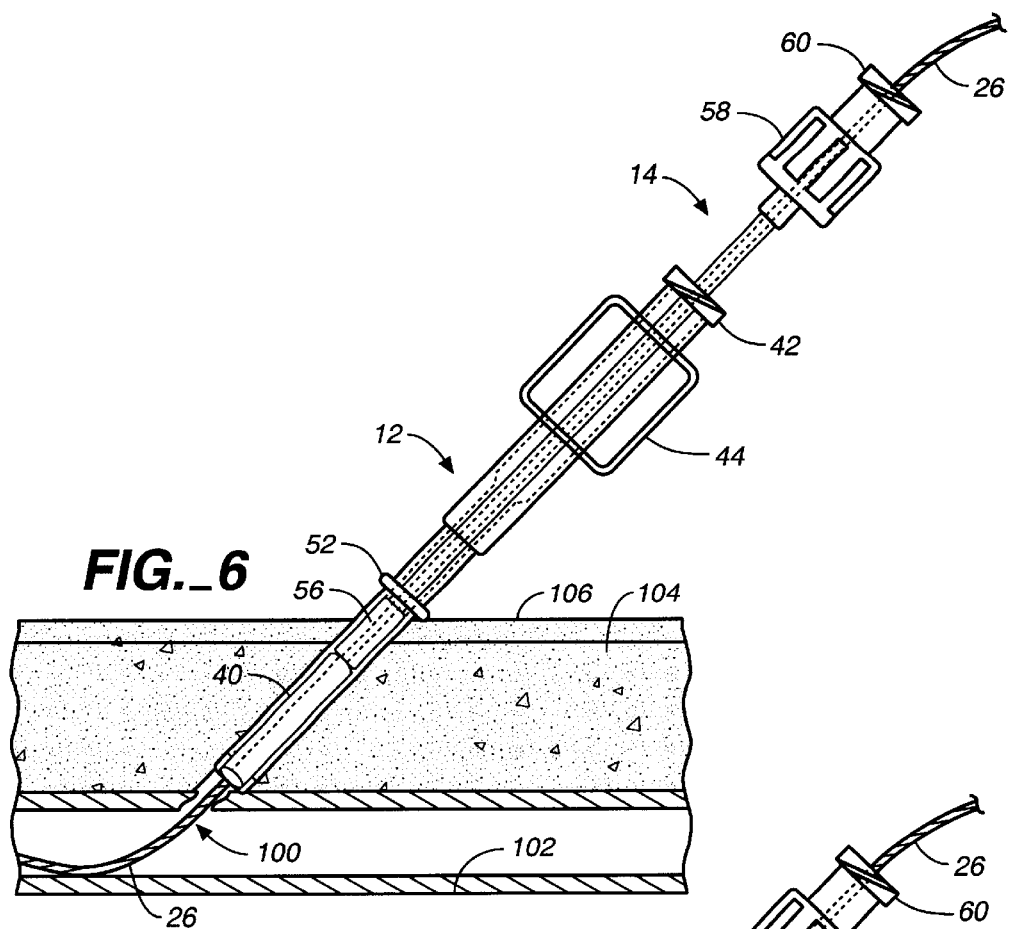
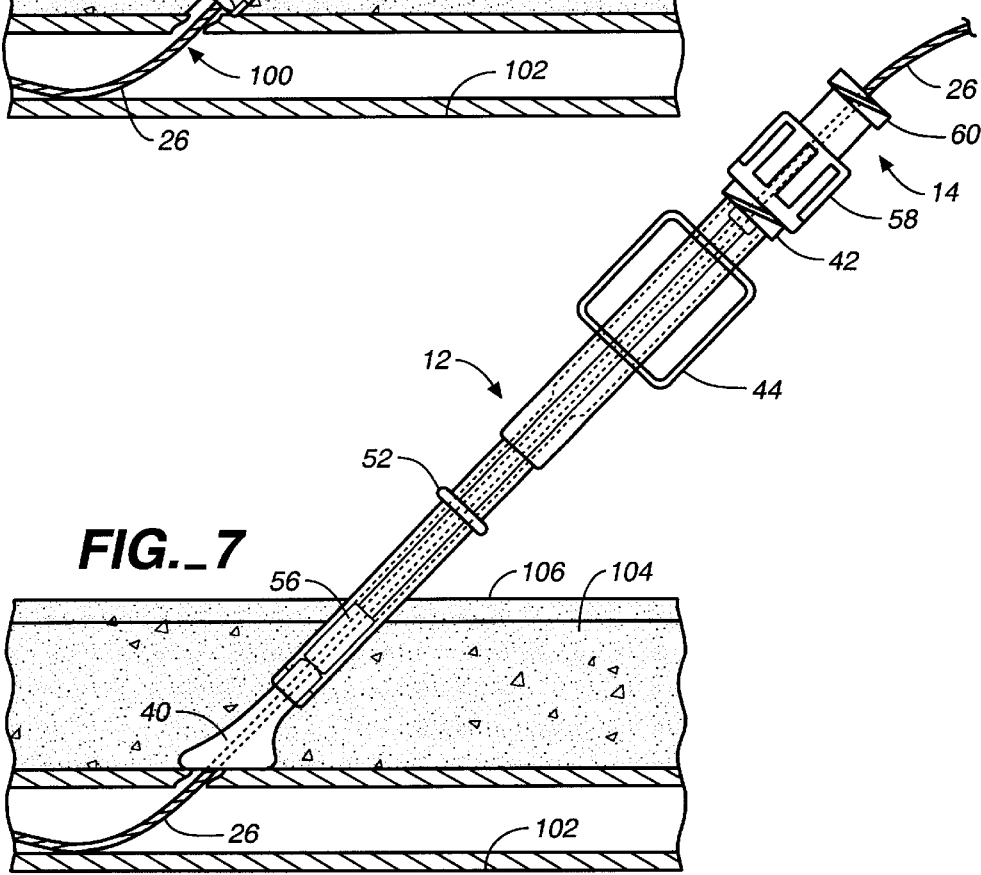

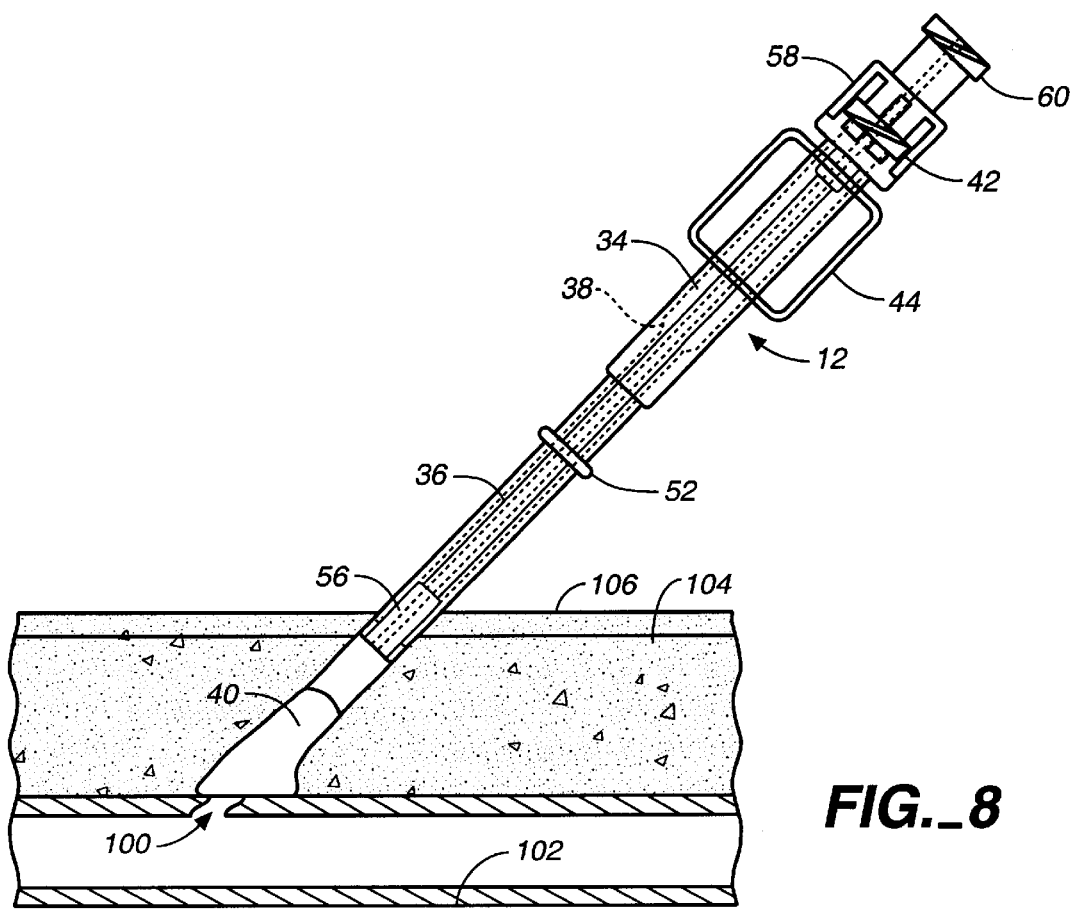
FIG._8
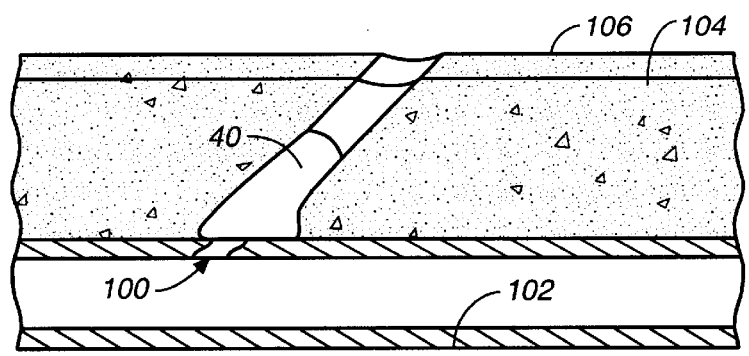
FIG._9

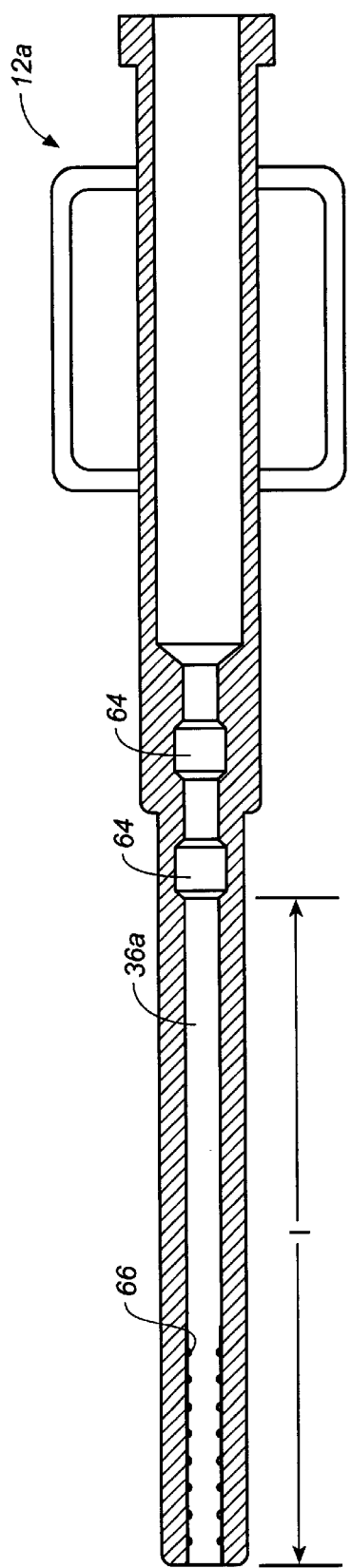
FIG._10
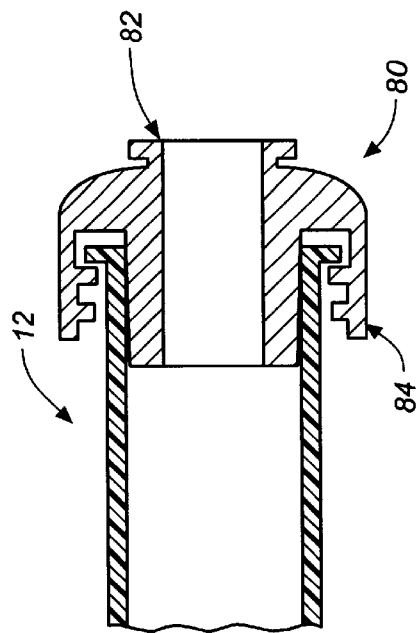
FIG._12
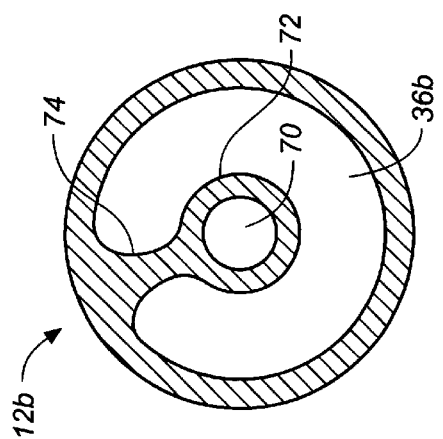
FIG._11

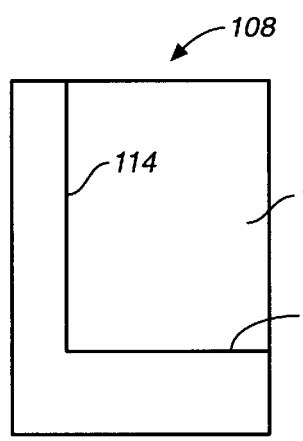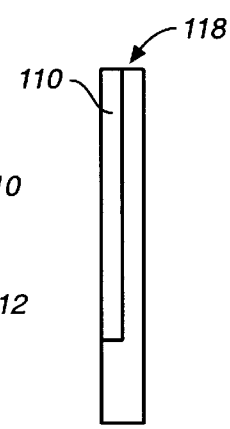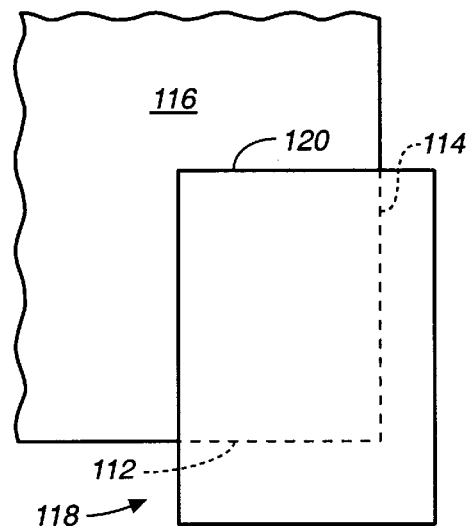
FIG._13     FIG._14     FIG._15
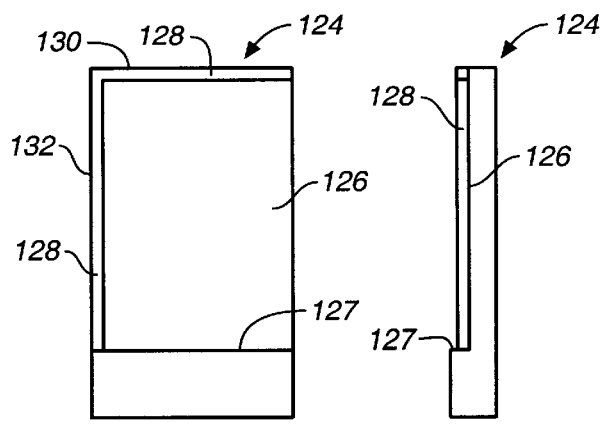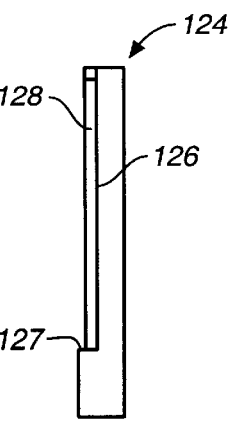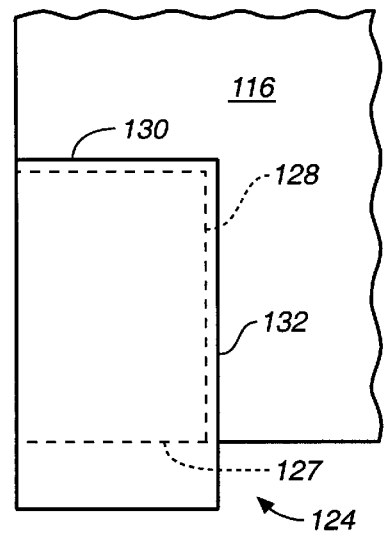
FIG._16     FIG._17     FIG._18

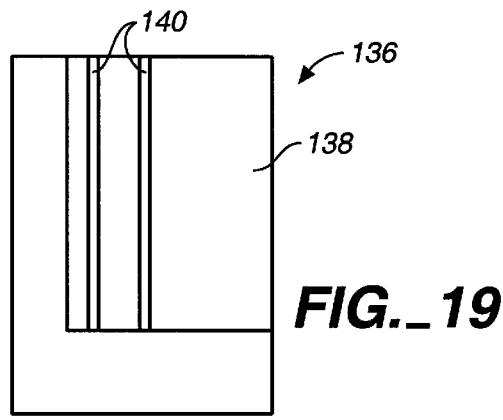
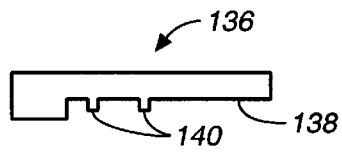
FIG._19
FIG._20
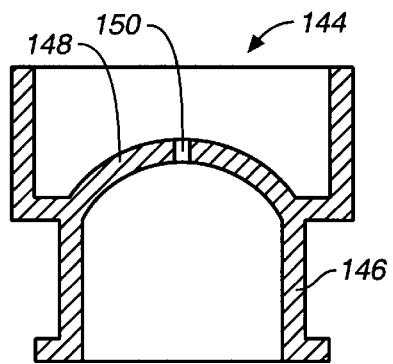
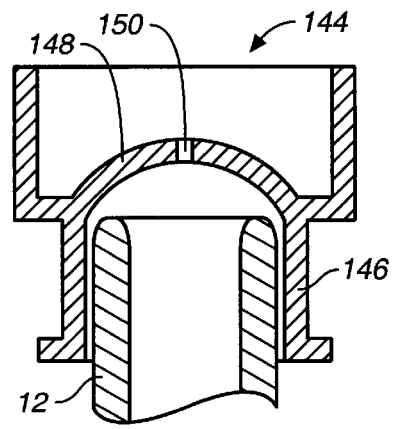
FIG._21
FIG._22
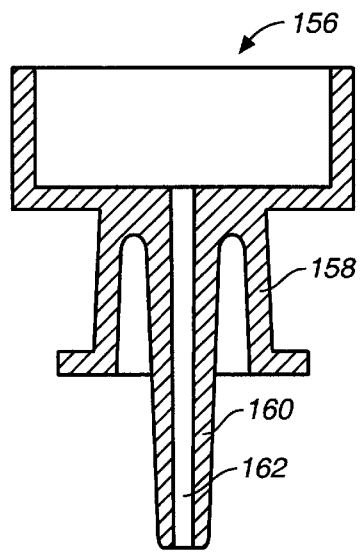
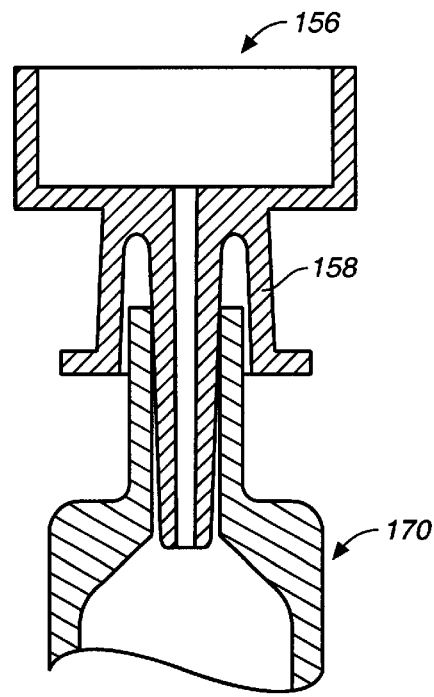
FIG._23
FIG._24

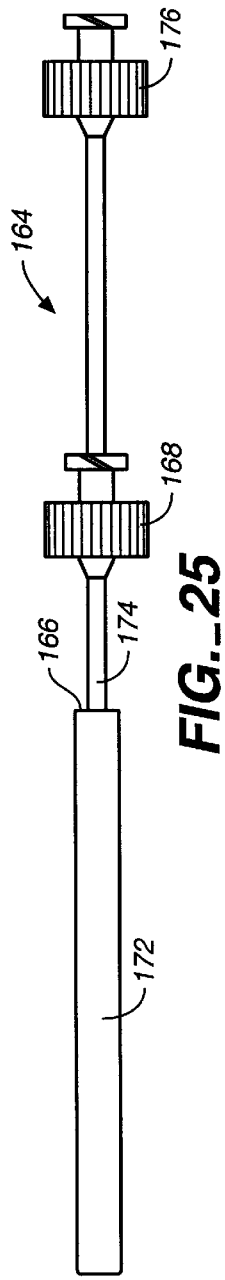
FIG._25
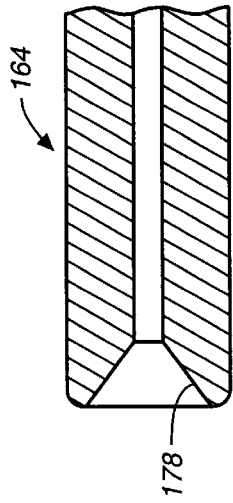
FIG._26
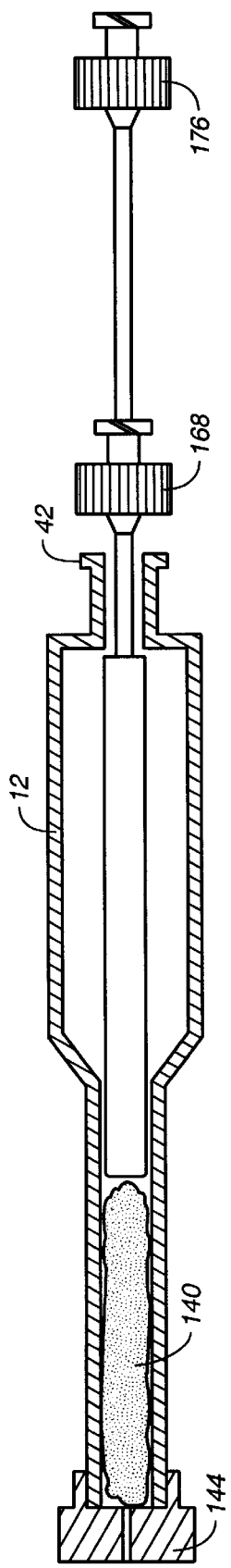
FIG._27

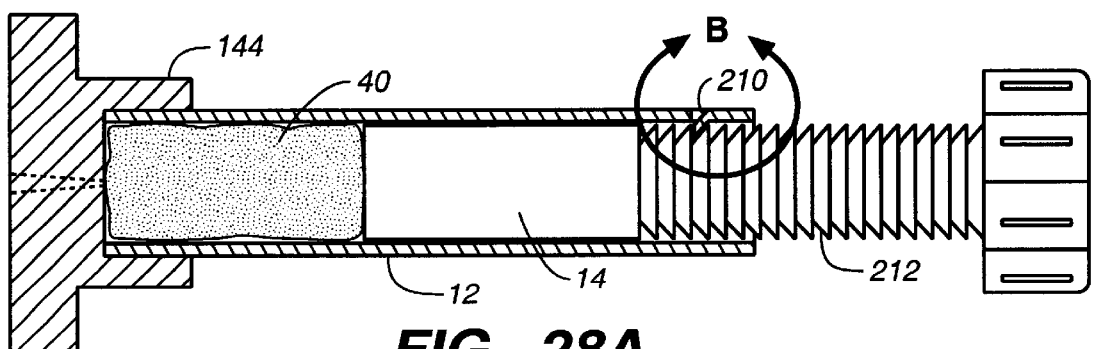
FIG._28A
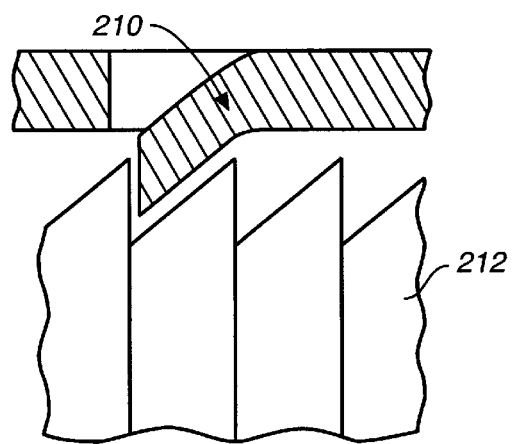
FIG._28B

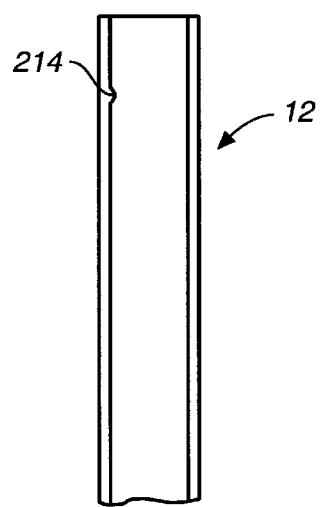
FIG._28C
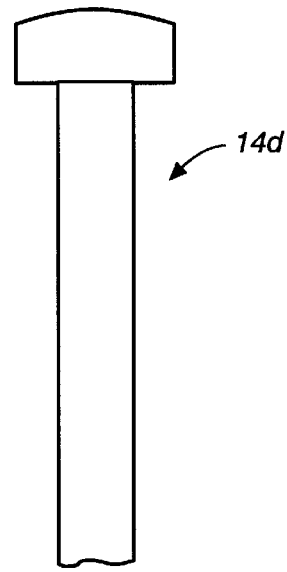
FIG._28D
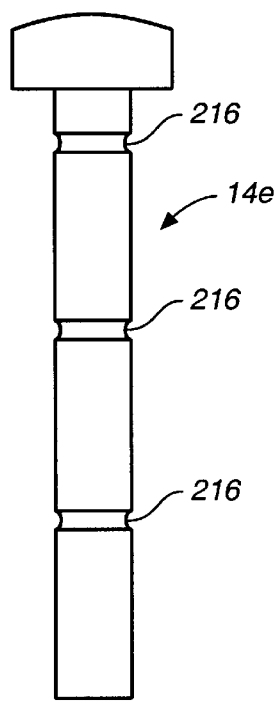
FIG._28E
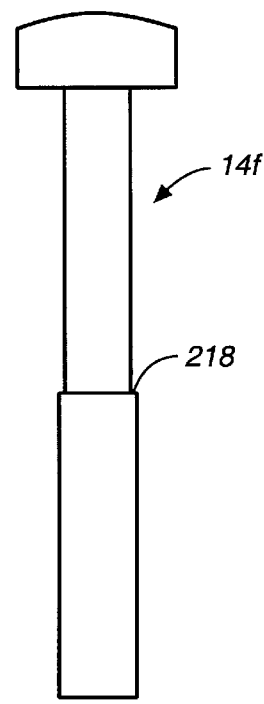
FIG._28F

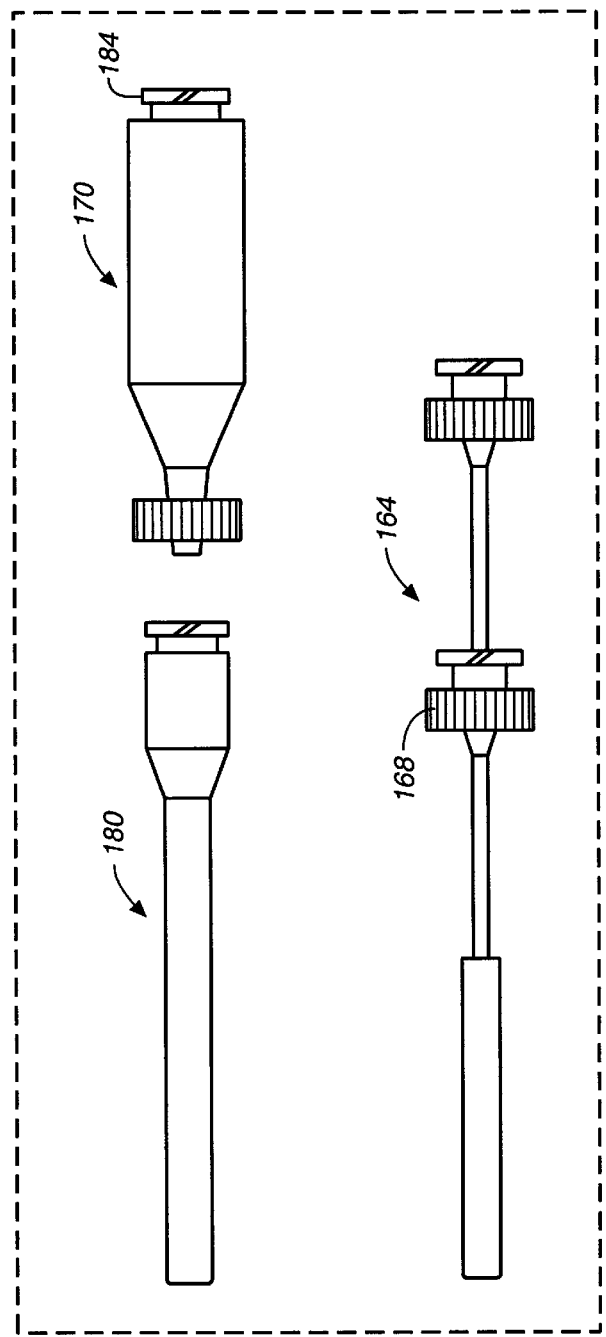
FIG._29
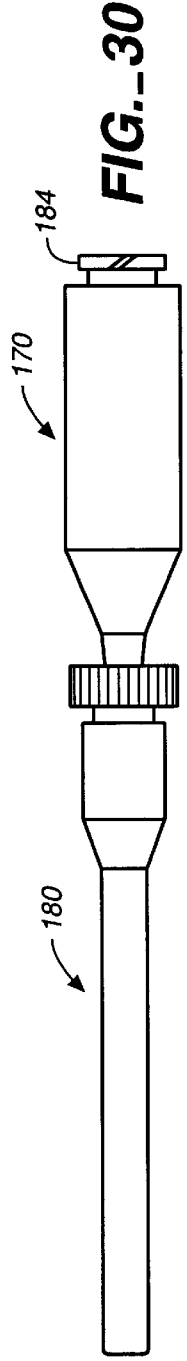
FIG._30
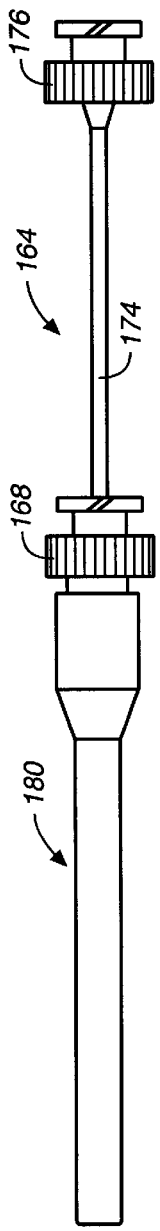
FIG._31

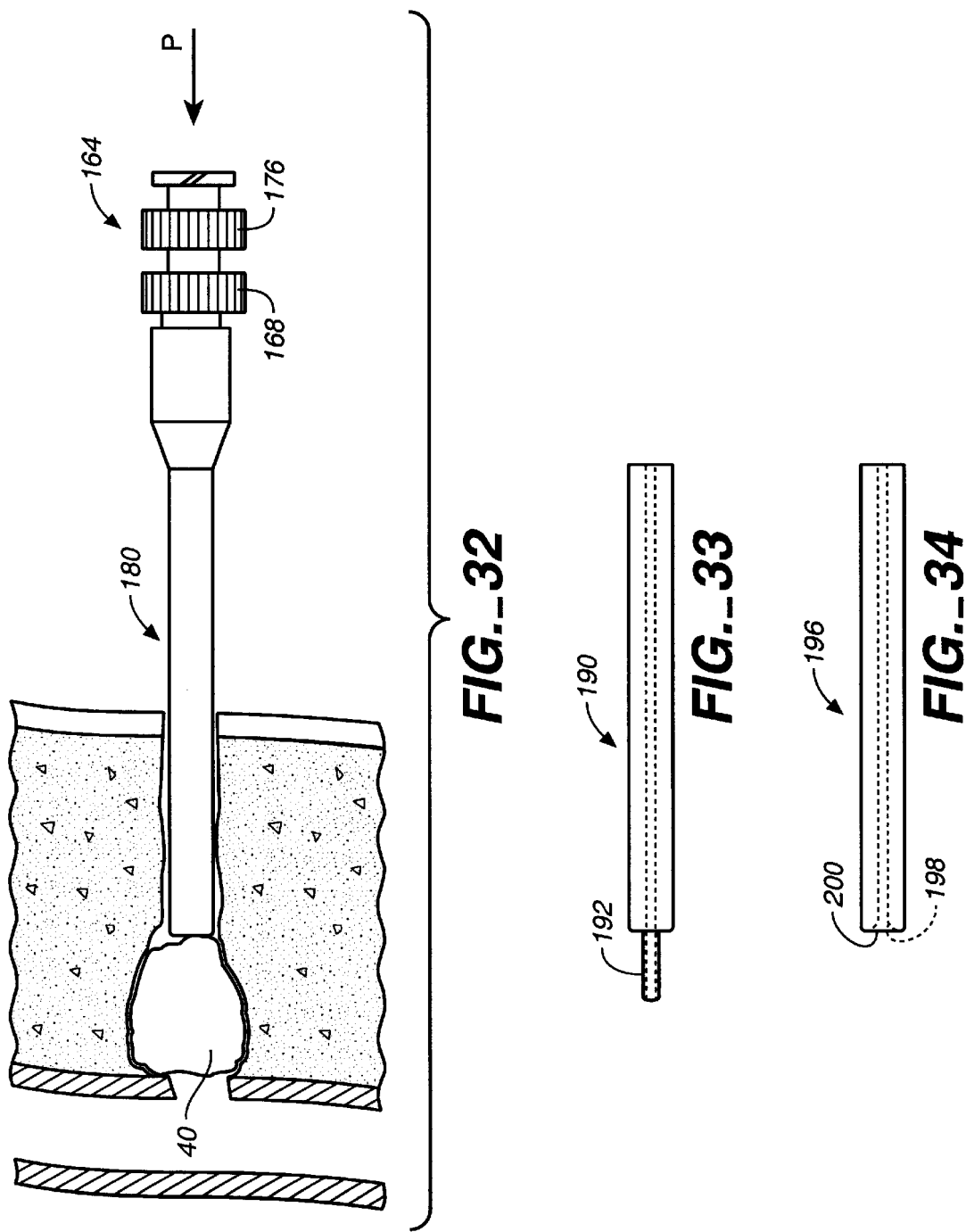

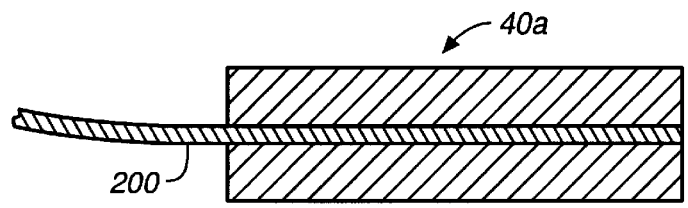
FIG._35
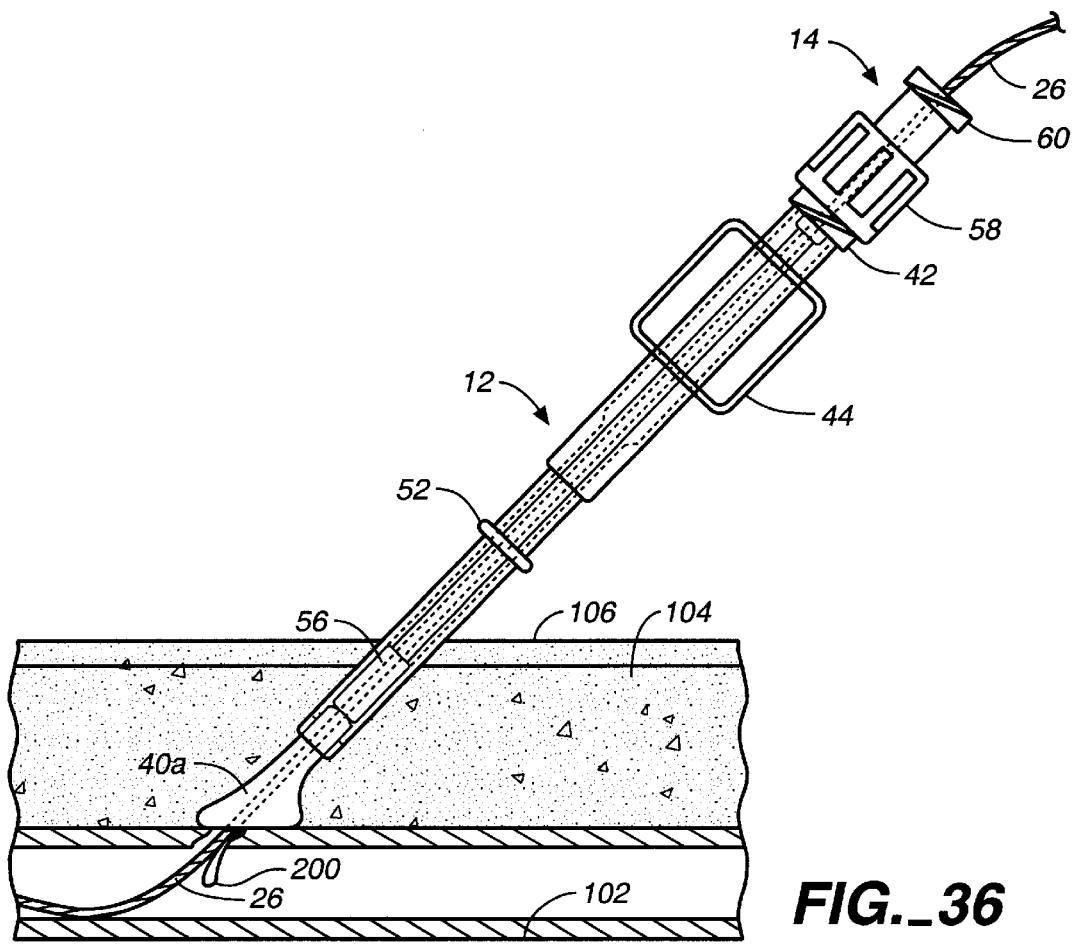
FIG._36

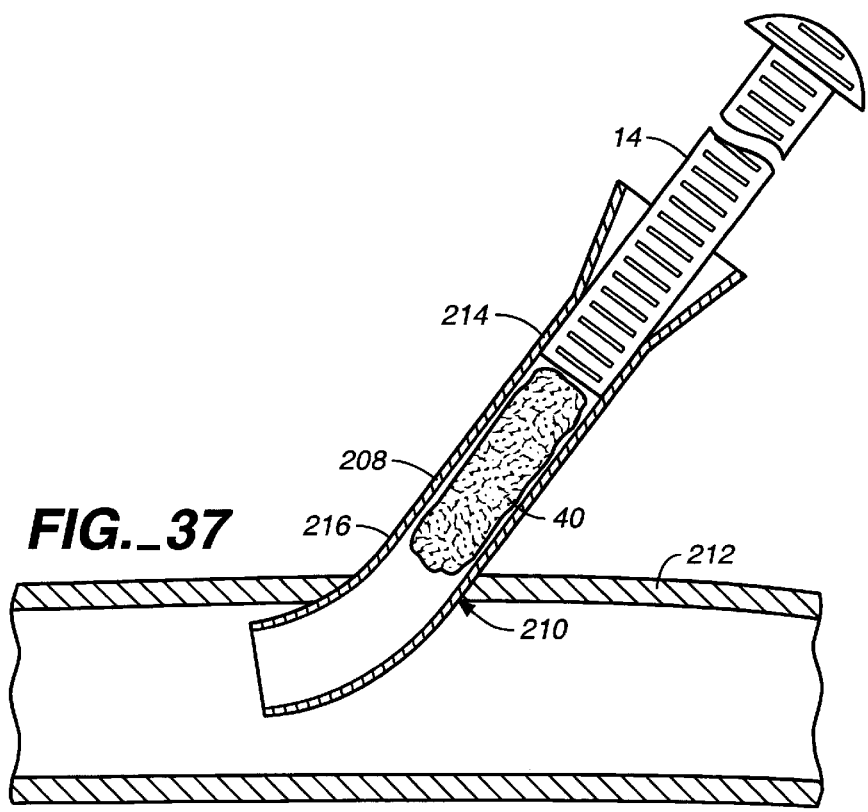
FIG._37
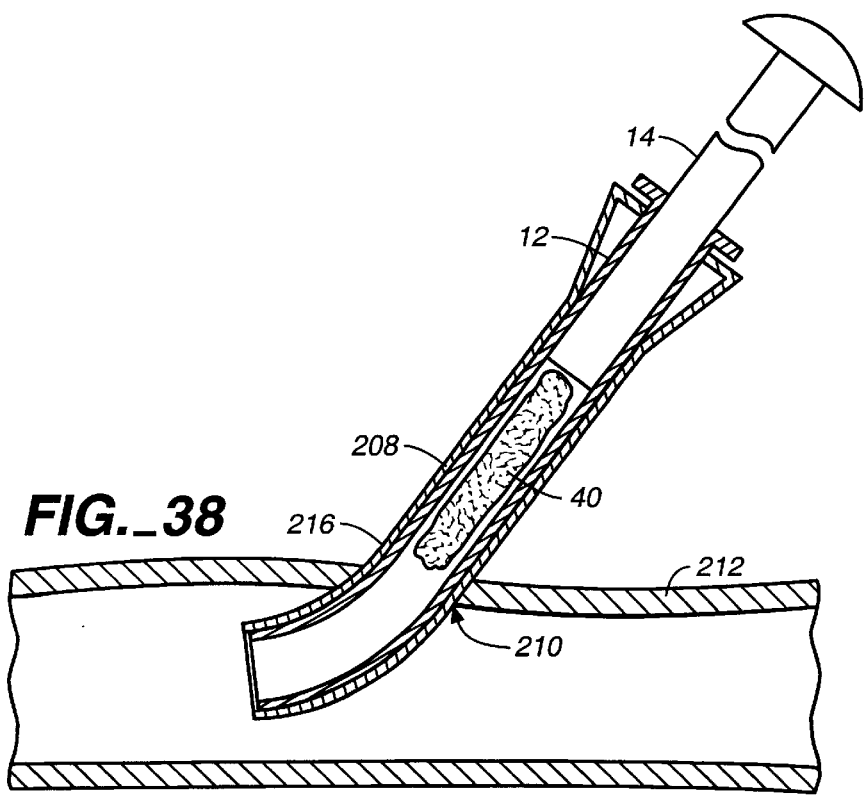
FIG._38

SYSTEM AND METHOD FOR FACILITATING HEMOSTASIS OF BLOOD VESSEL PUNCTURES WITH ABSORBABLE SPONGE

This application is a continuation-in-part of U.S. Ser. No. 09/071,284 filed May 1, 1998, which is incorporated herein by reference in its now U.S. Pat. No. 6,162,192.

BACKGROUND OF THE INVENTION

1. Field of the Invention

The invention relates to a closure system for blood vessel punctures, and more particularly, the invention relates to a system and method for facilitating hemostasis of blood vessel punctures with an absorbable sponge material.

2. Brief Description of the Related Art

A large number of diagnostic and interventional procedures involve the percutaneous introduction of instrumentation into a vein or artery. For example, coronary angioplasty, angiography, atherectomy, stenting of arteries, and many other procedures often involve accessing the vasculature through a catheter placed in the femoral artery or other blood vessel. Once the procedure is completed and the catheter or other instrumentation is removed, bleeding from the punctured artery must be controlled.

Traditionally, external pressure is applied to the skin entry site to stem bleeding from a puncture wound in a blood vessel. Pressure is continued until hemostasis has occurred at the puncture site. In some instances, pressure must be applied for a up to an hour or more during which time the patient is uncomfortably immobilized. In addition, a risk of hematoma exists since bleeding from the vessel may continue beneath the skin until sufficient clotting effects hemostasis. Further, external pressure to close the vascular puncture site works best when the vessel is close to the skin surface and may be unsuitable for patients with substantial amounts of subcutaneous adipose tissue since the skin surface may be a considerable distance from the vascular puncture site.

More recently, devices have been proposed to promote hemostasis directly at a site of a vascular puncture. One class of such puncture sealing devices features an intraluminal anchor which is placed within the blood vessel and seals against an inside surface of the vessel puncture. The intraluminal plug may be used in combination with a sealing material positioned on the outside of the blood vessel, such as collagen. Sealing devices of this type are disclosed in U.S. Pat. Nos. 4,852,568; 4,890,612; 5,021,059; and 5,061,274.

Another approach to subcutaneous blood vessel puncture closure involves the delivery of non-absorbable tissue adhesives, such cyanoacrylate, to the perforation site. Such a system is disclosed in U.S. Pat. No. 5,383,899.

The application of an absorbable material such as collagen or a non-absorbable tissue adhesive at the puncture site has several drawbacks including: 1) possible injection of the material into the blood vessel causing thrombosis; 2) a lack of pressure directly on the blood vessel puncture which may allow blood to escape beneath the material plug into the surrounding tissue; and 3) the inability to accurately place the absorbable material plug directly over the puncture site.

The use of an anchor and plug system addresses these problems to some extent but provides other problems including: 1) complex and difficult application; 2) partial occlusion of the blood vessel by the anchor when placed properly; and 3) complete blockage of the blood vessel or a branch of the blood vessel by the anchor if placed improperly. Another problem with the anchor and plug system involves reaccess. Reaccess of a particular blood vessel site sealed with an anchor and plug system is not possible until the anchor has been completely absorbed because the anchor could be dislodged into the blood stream by an attempt to reaccess.

Yet another approach to subcutaneous puncture closure involves the internal suturing of the blood vessel puncture with a specially designed suturing device. However, these suturing devices involve a significant number of steps to perform suturing and require substantial expertise.

Accordingly, it would be desirable to provide a system for facilitating hemostasis of blood vessel punctures which addresses the drawbacks of the known systems.

SUMMARY OF THE INVENTION

One aspect of the present invention relates to a device for facilitating hemostasis of a puncture in the wall of a blood vessel including an introducer for compressing a sponge pledget for delivery into a patient to seal the puncture, the introducer including a staging chamber with a first diameter configured to receive the absorbable sponge pledget, a delivery chamber with a second diameter smaller than the first diameter, and a tapered section between the staging chamber and the delivery chamber for compressing the pledget, and a plunger insertable into the introducer for ejection of the pledget from the delivery chamber into a patient to seal the puncture in the blood vessel wall.

In accordance with another aspect of the present invention, a method for facilitating hemostasis of a puncture in the wall of a blood vessel includes the steps of establishing a depth of a blood vessel puncture of a patient; loading an introducer with a sponge pledget by hydrating and compressing the pledget; loading the introducer over a guidewire positioned in the blood vessel by inserting the guidewire through the hydrated and compressed pledget; and ejecting the pledget adjacent the blood vessel puncture to facilitate hemostasis while maintaining the guidewire in place.

In accordance with an additional aspect of the present invention, a device for facilitating hemostasis of a puncture in the wall of a blood vessel includes a staging chamber for hydrating a sponge pledget in preparation for delivery of the pledget into a patient to seal the puncture, a delivery chamber for delivering the hydrated sponge pledget to the puncture, and a plunger insertable into the delivery chamber for ejection of the pledget from the delivery chamber into a patient to seal the puncture in the blood vessel wall. A distal end of the staging chamber having a tapered lumen and a proximal end of the delivery chamber connectable to the distal end of the staging chamber for delivery of the pledget from the staging chamber to the delivery chamber.

BRIEF DESCRIPTION OF THE DRAWINGS

The invention will now be described in greater detail with reference to the preferred embodiments illustrated in the accompanying drawings, in which like elements bear like reference numerals, and wherein:

FIG. 1 is a top view of a blood vessel puncture sealing kit;

FIG. 2 is a side cross sectional view of a punctured blood vessel and a tract dilator for locating the puncture;

FIG. 3 is a side view of an introducer and pledget prior to placement within the introducer;

FIG. 4 is a side view of an introducer having a pledget positioned within the introducer staging chamber and a syringe attached to the introducer;

FIG. 5 is a side view of the introducer and syringe with the pledget hydrated and advanced to a delivery chamber within the introducer;

FIG. 6 is a side cross sectional view of a punctured blood vessel with the introducer and plunger positioned for delivery of the pledget;

FIG. 7 is a side cross sectional view of a punctured blood vessel with the pledget being deposited at the puncture site;

FIG. 8 is a side cross sectional view of a punctured blood vessel with a hydrated and kneaded pledget deposited at the puncture site, the guidewire removed, and the delivery system being withdrawn;

FIG. 9 is a side cross sectional view of a punctured blood vessel with a hydrated and kneaded pledget facilitating hemostasis of the puncture site;

FIG. 10 is a side cross sectional view of an alternative embodiment of an introducer;

FIG. 11 is a cross sectional view of a distal end of an introducer according to another alternative embodiment having a central channel for receiving the guidewire;

FIG. 12 is a cross sectional side view of a distal end of an introducer with a connector for connecting a syringe;

FIG. 13 is a bottom view of a template for use in forming a pledget;

FIG. 14 is a side view of the template of FIG. 13;

FIG. 15 is a top view of the template of FIG. 13 as it is placed for cutting a piece of a sponge sheet for formation of the pledget;

FIG. 16 is a bottom view of an alternative embodiment of a template for use in forming a pledget;

FIG. 17 is a side view of the template of FIG. 16;

FIG. 18 is a top view of the template of FIG. 16 as it is placed for cutting a piece from a sponge sheet for formation of the pledget;

FIG. 19 is a bottom view of an alternative embodiment of a template having creasing ribs;

FIG. 20 is an end view of the template of FIG. 19;

FIG. 21 is a side cross sectional view of a vent cap;

FIG. 22 is a side cross sectional view of the vent cap of FIG. 21 positioned on the distal end of a delivery chamber;

FIG. 23 is a side cross sectional view of an alternative embodiment of a vent cap;

FIG. 24 is a side cross sectional view of the vent cap of FIG. 23 positioned on a staging chamber;

FIG. 25 is a side view of a pusher for use in the present invention having a proximal stop and a sliding luer;

FIG. 26 is a side cross sectional view of the distal end of a pusher having a funnel shaped distal lumen;

FIG. 27 is a side view partially in cross section of an introducer with the pusher of FIG. 25;

FIG. 28a is a side cross sectional view of an introducer with a pusher having a rachet system; FIG. 28b is an enlarged view of the detail B of FIG. 28a showing the ratchet teeth and tab; FIG. 28c is a side cross sectional view of an introducer with a detent; FIGS. 28d–f are side views of pushers for use with the introducer of FIG. 28c;

FIG. 29 is a top view of a pledget delivery system including a two piece introducer with separate staging and delivery chambers;

FIG. 30 is a side view of the assembled introducer of FIG. 29 for delivery of the pledget from a staging chamber to the delivery chamber;

FIG. 31 is a side view of the delivery chamber with the pusher connected to the delivery chamber for delivery of the pledget;

FIG. 32 is a side view of the delivery chamber and pusher after delivery of the pledget;

FIG. 33 is a side view of a distal end of the dilator having a distal protrusion for strain relief;

FIG. 34 is a side view of a distal end of a dilator having a distal lumen providing a strain relief feature;

FIG. 35 is a side cross sectional view of a pledget with a rapidly dissolvable tip;

FIG. 36 is a side cross sectional view of a punctured blood vessel with the pledget of FIG. 35 being deposited;

FIG. 37 is a schematic side view of a system for delivering a pledget through a sheath; and FIG. 38 is a schematic side view of an alternative system for delivering a pledget through a sheath.

DETAILED DESCRIPTION OF THE PREFERRED EMBODIMENTS

An over the wire delivery system delivers an absorbable sponge pledget in a hydrated condition to a blood vessel puncture site to achieve hemostasis. One embodiment of the over the wire delivery system includes a tract dilator 10, an introducer 12, and a pusher 14, illustrated in kit form in FIG. 1. The system allows over the wire delivery of the absorbable sponge material directly to the puncture site to achieve hemostasis. Over the wire delivery ensures that the sponge material is properly positioned to fully occlude the puncture. In addition, the absorbable sponge material is delivered in a hydrated state which immediately expands to stop blood flow through the puncture. The introducer allows the delivery of more absorbable sponge material through a smaller tract by hydrating and compressing the absorbable sponge material.

Prior to discussing the present invention in further detail, the following terms are defined:

"Pledget" means a piece of sponge formed into a generally elongated shape having a size which allows delivery in a hydrated state through a delivery cannula or introducer to a site of a puncture in a blood vessel.

"Sponge" means a biocompatible material which is capable of being hydrated and is resiliently compressible in a hydrated state. Preferably, the sponge is non-immunogenic and may be absorbable or non-absorbable.

"Absorbable sponge" means sponge which when implanted within a human or other mammalian body is absorbed by the body.

"Hydrate" means to partially or fully saturate with a fluid, such as, saline, water, contrast agent, thrombin, therapeutic agents, or the like.

"Kneading" of the absorbable sponge material means both dry and wet manipulation of sponge material which compresses, enlarges, or changes the shape of the sponge material causing the sponge material to have improved expansion response.

As shown in FIG. 1, the tract dilator 10, the introducer 12, and the pusher 14 may be provided to a medical facility in the form of a kit or individually. The tract dilator 10 as illustrated in FIGS. 1 and 2 includes a distal tip 20, a proximal end 22, and a lumen 24 extending from the distal tip to the proximal end of the tract dilator. The lumen 24 is provided to allow the tract dilator 10 to be received over a guidewire 26 which extends through the puncture wound 100 into the blood vessel 102. The tract dilator 10 may have a constant cross section or may taper slightly to a smaller diameter at the distal tip 20. According to an alternative embodiment, the tract dilator 10 may have a narrow shaft with an enlarged distal tip. The distal tip 20 has rounded edges to prevent catching on subcutaneous tissue 104 as the tract dilator 10 is inserted through the skin 106 and tissue to the blood vessel puncture site. The tract dilator distal tip 20 has a diameter such that the tip of the tract dilator will not pass into the blood vessel but will stop and provide tactile feedback when it reaches the external blood vessel wall 102. Other embodiments of tract dilators will be discussed below with respect to FIGS. 33 and 34.

A depth indicator 30 is positioned around the tract dilator 10 and is movable in an axial direction. Once the tract dilator 10 has been inserted until the distal tip 20 abuts the external wall of the blood vessel 102, as shown in FIG. 2, the depth indicator 30 is manually positioned adjacent the patient's skin 106. Alternatively, the depth indicator 30 can be pushed to a depth indicating position by the skin 106 as the dilator is inserted. Preferably, the depth indicator 30 is an elastic ring which is movable axially on the tract dilator 10 and maintains a measured position for comparison with the introducer 12.

A side view of an introducer 12 is illustrated in FIGS. 1 and 3. The introducer 12 includes a staging chamber 34 for receiving an absorbable sponge pledget 40 and a delivery chamber 36 for receipt of a hydrated and compressed pledget from the staging chamber. A tapered section 38 is provided between the staging chamber 34 having a larger diameter lumen and the delivery chamber 36 having a smaller diameter lumen. The tapered section 38 of the introducer 12 acts as a compression member to compress the hydrated pledget 40 into the delivery chamber. The introducer 12 also includes a luer fitting 42 at a proximal end for connection to a conventional syringe and wing members 44 for use in grasping the introducer. A two part introducer having separate delivery and staging chambers will be discussed below with respect to FIGS. 29–31.

The absorbable sponge pledget 40 according to one preferred embodiment of the invention is formed from a sheet of absorbable sponge material which has been cut into a rectangular shape and rolled to form a compact, substantially cylindrical, elongated pledget. The pledget 40 is sized to be received within the staging chamber 34 of the introducer 12 in a dry rolled state. Templates for use in forming the pledget 40 are shown in FIGS. 13–20.

Once the pledget 40 has been inserted into the staging chamber 34 of the introducer 12, a conventional syringe 50 containing a hydrating fluid is connected to the luer fitting 42, as shown in FIG. 4. The pledget 40 is then hydrated within the staging chamber 34 by injecting a fluid into the staging chamber from the syringe 50 causing the pledget to swell, partially or fully blocking the lumen of the introducer. The partial hydration or wetting of the exterior surface of the pledget 40 creates a lubricous surface on the pledget. The hydrated pledget 40 is then forced into the delivery chamber 36 by injecting additional fluid with the syringe 50 to force the pledget through the tapered section 38 to the delivery chamber 36. For a somewhat smaller pledget 40 which does not entirely block the lumen of the introducer 12 after hydrating, the venturi effect will help to draw the pledget into the delivery chamber 36.

As shown in FIG. 5, a finger may be placed over the distal end of the introducer 12 during delivery of the pledget 40 to the delivery chamber 36 to prevent the pledget from being ejected from the introducer by the pressure of the fluid. Preferably, one or more vent holes 46 are provided in the side walls of the introducer adjacent the distal tip to allow air and liquid to escape from the introducer while the pledget 40 is positioned for delivery. These vent holes 46 are small enough to prevent the pledget 40 from passing substantially into the vent holes.

As an alternative to placement of a finger at the distal end of the introducer 12 during advancement of the pledget 40 into the delivery chamber, a removable vent cap may be used as described below with respect to FIGS. 21–24. Further, the vent holes 46 may be omitted and a screen or a cap having a screen may be used to allow fluid to pass through the screen while the screen prevents the pledget 40 from being ejected.

Another alternative method for positioning the pledget adjacent the distal end of the delivery chamber is to provide a proximal vent hole in the side wall of the delivery chamber. The proximal vent hole is positioned such that when the pledget has moved to the distal end of the delivery chamber, the pledget is substantially clear of the proximal vent allowing additional injected fluid to pass out of the delivery chamber through the vent. According to this method, the proximal vent acts as a fluid release valve to prevent further advancement of the pledget once the pledget has reached a desired position.

The introducer 12 also includes a depth indicator 52 which is an axially movable member used to indicate the depth to which the introducer should be inserted into the patient to achieve the proper positioning of the pledget 40 at the puncture site. The depth indicator 52 of the introducer 12 is aligned with the depth indicator 30 on the tract dilator 10 to achieve proper pledget delivery positioning.

The introducer 12 may be formed in any known manner such as by injection molding from a plastic material. Preferably, the introducer 12 is transparent so that the pledget 40 can be viewed through the introducer and the user can visually confirm the pledget position. The introducer lumen may be provided with a friction reducing coating for improved pledget delivery. The delivery fluid also reduces friction for improved delivery by wetting the exterior surface of the pledget.

The pusher 14, as illustrated in FIG. 1, includes a distal end 56 which is configured to slide within the lumen of the delivery chamber 36 of the introducer 12. Preferably, there is a very small clearance or a resilient interference between the outer diameter at the distal end 56 of the pusher 14 and the inner diameter of the delivery chamber 36 to prevent portions of the pledget from getting caught between the pusher and the introducer 12. A resilient pusher distal end 56 or a sealing member on the pusher 14 may be used to accomplish or approach a resilient fit between the introducer 12 and the pusher.

The pusher 14 also may include a fitting 58 for connecting the proximal end of the pusher to the proximal end of the introducer 12. The fitting 58 acts as a stop to limit the motion of the pusher 14 with respect to the introducer 12. When the pusher 14 is locked to the introducer 12, the two may be used together to apply localized compression to the puncture site. A female luer fitting 60 may also be included at the proximal end of the pusher 14 for connection of a syringe to the pusher for injection of beneficial agent through the pusher.

One method of delivering an absorbable sponge pledget 40 to facilitate hemostasis of a blood vessel puncture wound will now be described with respect to the steps illustrated in FIGS. 2–9. After an intravascular procedure has been completed, a guidewire 26 is already in place passing through the subcutaneous tissue into the blood vessel. Alternatively, if a guidewire is not already in place the guidewire is inserted through an access sheath used in the intravascular procedure and the access sheath is then removed. The guidewire 26 is maintained in place with a proximal end extending from the patient's body and a distal end extending through the skin 106 and subcutaneous tissue 104, through the blood vessel puncture 100, and into the blood vessel 102. As discussed above, the tract dilator 10 is threaded over the guidewire 26 and advanced down through the subcutaneous tissue 104 to an outside surface of the blood vessel 102. Resistance is felt when the tract dilator distal tip 20 contacts the exterior of the blood vessel and the tract dilator will not easily pass though the vessel puncture 100 and into the vessel. The depth indicator 30 on the tract dilator 10 is moved to abut the skin surface 106 indicating a distance from the skin surface to the blood vessel puncture site. The tract dilator 10 is then removed over the guidewire 26 and the introducer depth indicator 52 is aligned with the tract dilator depth indicator 30.

A sheet of absorbable sponge material is cut into a rectangle, is rolled tightly to form a pledget 40, and is placed into the staging chamber 34 of the introducer 12. The steps of cutting and rolling the pledget 40 and placing the dry pledget in the introducer staging chamber 34 may be performed before or after the intervascular procedure. Alternatively, the introducer 12 may be provided preloaded with a prepared pledget 40. With the pledget 40 placed in the introducer, the syringe 50 is filled with a hydrating fluid such as saline, thrombin, contrast agent, other therapeutic agent, or the like and attached to the introducer 12 as illustrated in FIG. 4. Fluid is injected slowly into the introducer 12 to hydrate the pledget 40. The user then pauses to allow hydration and initial swelling of the pledget 40. Sufficient hydration may occur in about 20 to 30 seconds or less depending on the size of the pledget 40.

As shown in FIG. 5, the user then places a finger over the distal end of the introducer 12 and injects fluid with the syringe 50 to force the pledget 40 through the tapered section 38 and into the smaller end or delivery chamber 36 of the introducer 12. Injection of fluid is stopped when the pledget 40 is positioned at the distal end of the delivery chamber 36. At this point the syringe 50 is removed and the introducer is loaded over the proximal end of the guidewire 26 for the delivery of the pledget 40 to the puncture site.

As shown in FIG. 6, a proximal end of the guidewire 26 is fed into the distal end of the introducer 12 though the hydrated and compressed pledget 40 and out the proximal end of the introducer. Preferably, the guidewire 26 is fed through substantially the center of the pledget 40 to ensure that the implanted pledget is centered over the blood vessel puncture 100. Alternatively, the guidewire may be inserted along a side of the pledget 40, through a separate second lumen of the introducer, through an axial lumen in the pledget, or through a low density center of the pledget.

After feeding the guidewire 26 through the introducer, the guidewire 26 is fed through the pusher 14 and the pusher is advanced into the introducer until the distal end 56 of the pusher is in contact with the pledget 40. The introducer 12 and pusher 14 are then advanced together down though the skin 106 and the subcutaneous tissue 104 until the depth indicator 52 on the exterior of the introducer is at the skin level.

In the step illustrated in FIG. 7, the pusher 14 is held stationary while the introducer 12 is withdrawn proximally preferably to a distance of about 75% of the length of the compressed, hydrated pledget 40. This 75% withdrawal distance may be indicated with an appropriate marker on the introducer 12 or the plunger 14 or by contact between the fittings 42, 58 of the introducer and plunger. The portion of the pledget 40 ejected into the tissue quickly expands upon delivery to fill the available space and provide localized compression. With the pusher 14 and introducer 12 in the position illustrated in FIG. 7 and the pledget 40 partially ejected, a slight forward pressure is maintained by the operator on the introducer and pusher to increase local compression for a period of time of approximately 1 minute to allow hemostasis to begin. The forward pressure causes the pledget 40 to be compressed around the puncture site, as shown in FIG. 7. The guidewire 26 is then completely removed from the introducer 12 and the pusher 14. The introducer 12 is withdrawn the remaining approximately 25% by engaging the fitting 58 of the pusher with the female luer fitting 42 of the introducer to completely discharge the pledget 40 into the subcutaneous tissue 104 above the puncture site 100. A slight forward pressure can then be maintained by the operator on the introducer 12 and pusher 14 for approximately 1 minute before the introducer and pusher are removed from the tissue tract leaving the absorbable sponge pledget 40 positioned against the outer vessel wall, as shown in FIG. 9, providing local compression and facilitating hemostasis. The delivered pledget 40 maintains hemostasis until healing of the blood vessel 102 occurs. The pledget 40 is absorbed by the body over time.

One type of absorbable sponge material which is acceptable for use in the present invention is Gelfoam, manufactured by the Upjohn Company. Gelfoam is a porous, pliable, cross-linked gelatin material and is available commercially in sheet form as pre-compressed or non-compressed sponge. The material may be provided preformed as a pledget 40 or may be cut with a punch, or a stencil or template and knife and rolled to form a pledget as described above. Once hydrated, the pledget 40 can be easily compressed to fit into a lumen having a smaller cross sectional area than the original cross sectional area of the pledget. Additionally, the kneading of the hydrated pledget 40 during delivery encourages air trapped within the Gelfoam to be expelled and replaced with fluid, allowing rapid expansion upon delivery. When a pledget 40 of a pre-compressed Gelfoam is hydrated and kneaded (expelling air) during delivery, the pledget will have the absorption capacity to rapidly expand to many times (e.g., 3 or more times) its original dry volume upon delivery. When a pledget 40 of the non-compressed Gelfoam is hydrated and kneaded (expelling air) during delivery, the pledget will have the absorption capacity to rapidly expand to its original dry volume upon delivery. These properties make the Gelfoam sponge material particularly useful for facilitating hemostasis of puncture wounds by injection.

Abrupt lumen diameter changes within the introducer 12, such as at the tapered section 38, will improve "kneading" of the absorbable sponge material passing through the introducer. Manipulation of the dry absorbable sponge material, such as the rolling of the pledget 40, also provides kneading. Kneading improves hydration of the sponge material thereby improving the expansion properties of the hydrated delivered absorbable sponge.

According to alternative embodiments of the introducer, enlarged, recessed, or irregular areas in the lumen of the introducer are provided to impart additional kneading action to the absorbable sponge material further improving expansion properties of the sponge. FIG. 10 illustrates one such alternative embodiment of the introducer 12a in which the delivery chamber of the introducer is provided with two enlarged areas 64. As the absorbable sponge pledget 40 passes through the enlarged areas 64 of the introducer 12*a*, the material expands and is compressed by the introducer to increase kneading of the pledget. According to another alternative embodiment, the introducer may be provided with a plurality of staggered irregularities for improved kneading of the absorbable sponge pledget 40. The irregularities, enlargements, or recesses will preferably have a relatively smooth surface to prevent the absorbable sponge material from becoming caught as it passes through the introducer. Preferably, a length "l" between a distal end of the introducer 12 and the distal most of the irregularities, enlargements, or recesses is sufficient to accommodate the entire hydrated, compressed pledget such that the pledget 40 will not become trapped between the plunger and the enlargements.

Another alternative embodiment for improved kneading of the pledget 40 includes features on the guidewire, such as, irregularities, curves, bends, or the like. The guidewire kneading features will improve kneading of the pledget 40 as the guidewire 26 is inserted through the pledget.

In addition to kneading, pledget delivery is enhanced by super hydration or rapid hydration of the pledget at high pressure. Rapid hydration may be accomplished by high pressure injection of a fluid into the introducer 12 while placing a finger or vent cap over the distal end of the introducer. Super hydration can also be achieved by placing the introducer 12, with the pledget 40 inside, into a pressurized container of fluid. Preferably, fluid pressures of 5 psi or greater are used for super hydration of the sponge material. This super hydration provides rapid and complete hydration of the material in preparation for use.

The embodiment of FIG. 10 also includes a delivery chamber 36*a* provided with internal barbs 66 which help to retain the compressed pledget 40 positioned adjacent the distal end of the introducer 12*a* while the guidewire 26 is inserted through the pledget material. The internal barbs 66 are small enough to not cause interference with the passage of the pusher. The barbs 66 help to hold the pledget 40 in place as the guidewire 26 is inserted through the pledget. In addition to or in place of the internal barbs 66, other features may be used, such as ribs, a textured surface, holes, or the like. One example of an alternative structure for retaining the pledget 40 at the distal end of the introducer 12*a* during insertion of the guidewire is a distal counterbore (not shown). The counterbore may be formed by cutting a bore in from the distal end of the introducer 12*a* which is coaxial with the introducer lumen and has a diameter which is slightly larger than the diameter of the introducer lumen. The counterbore may have a length which is approximately the length of the pledget 40 or smaller. Preferably, the length of the counterbore is approximately $2/3$ to $1/2$ the length of the pledget 40.

The barbs 66, counterbore, and other retention features are particularly useful when using a conventional coiled guidewire which creates a significant amount of friction when threaded through the absorbable sponge material. Alternatively, a smooth, solid shaft guidewire, a plastic sheathed guidewire, or a hydrophilically coated guidewire can be used. These smooth guidewires are more easily threaded through the absorbable sponge material. A guidewire with a reduced diameter proximal portion will also facilitate threading of the guidewire 26 through the pledget 40.

As an alternative to the barbs 66 or a specially designed guidewire, the plunger 14 can be used to hold the pledget 40 in place during threading of the guidewire 26 through the pledget. A hydraulic back pressure can also be created to hold the pledget 40 in place by blocking the proximal end of the introducer 12, such as by the user's finger. Such a hydraulic back pressure will help to hold the pledget in place in the delivery chamber.

Although the use of a tract dilator 10 has been described above, the introducer 12 can be used in place of the dilator and the depth determining step can be performed while inserting the introducer, particularly where a plastic sheathed guidewire, other friction reducing guidewire, or other friction reducing feature is used. The use of the introducer 12 as the dilator eliminates errors which may occur in accurately setting the depth indicator 52 on the introducer.

According to one embodiment of the invention, the pusher 14 is inserted within the introducer 12 and the luer fitting 58 at the proximal end of the pusher is attached to the luer fitting 42 on the introducer. This introducer/pusher system is advanced over a guidewire into the tissue tract to establish the location of the exterior wall of the blood vessel. The exterior wall of the blood vessel is palpitated with the introducer/pusher system and the depth indicator 52 on the introducer is set at the skin level.

According to an alternative embodiment, an introducer/pusher system may be used for dilation in which the pusher 14 or obturator used during dilation is different from the pusher which is used for delivery of the pledget. The pusher 14 for use during dilation preferably has a luer lock at a proximal end which locks to the proximal end of the introducer 12 and has a length such that the distal ends of the pusher and introducer are aligned. After setting of the depth indicator 52, the system is then removed from the tissue tract and the pusher 14 is removed from the introducer 12. The introducer 12 is then prepared for delivery of the pledget 40 by hydrating and staging the pledget within the introducer. The introducer 12 is then reintroduced over the guidewire and advanced into the tissue tract to the depth indicated by the depth indicator 52. In this manner, reliable, accurate, and repeatable placement of the pledget 40 is performed without the use of a separate tract dilator.

According to another embodiment of the invention, the introducer is inserted to the pledget delivery site through a sheath. In this method, the sheath with a removable dilator positioned inside the sheath is advanced over the guidewire into a tissue tract to establish the location of an arterial puncture site. Once the exterior wall of the vessel has been located by palpating, the dilator is withdrawn leaving the sheath in place. The introducer 12 with prepared pledget 40 and pusher 14 are then inserted into the sheath over the guidewire. The introducer 12 may be locked to the sheath, such as by a luer lock. This will position the distal end of the introducer 12 at the distal end of the sheath in preparation for pledget delivery. The combined sheath and introducer system is used to deposit the pledget in the manner described above.

Alternatively, a sheath such as the sheath which was used during the procedure may be used for delivery of the pledget. For delivery of the pledget through the sheath, the sheath is first positioned adjacent the exterior of the blood vessel either by palpating with the sheath and an internal dilator or by any of the known visualization methods such as fluoroscopy. The sheath may be preloaded with the pledget or the pledget may be loaded after sheath positioning. The pledget is delivered by inserting a plunger into the sheath and withdrawing the sheath over the plunger to deposit the pledget adjacent the exterior of the blood vessel.

For preloading the sheath with the pledget, a staging chamber is attached to the proximal end of the sheath and the pledget is advanced by fluid injection to the distal end of the sheath. The pledget may be positioned properly by use of a distal vent or vent cap which allows excess fluid to escape as discussed above. Alternatively, a proximal vent may be provided in the sheath at a location which corresponds to a proximal end of the pledget when the pledget is positioned at a distal end of the sheath. Once the pledget has been advanced so the proximal end of the pledget is at or past the proximal vent, the fluid will exit through the vent in the side of the sheath preventing further advancement of the pledget. The sheath with the pledget loaded at the distal end is then inserted over the guidewire to the puncture site and a plunger is used to deploy the pledget.

When the sheath is used for delivery of the pledget without first removing the sheath from the tissue tract, the sheath is withdrawn until a distal tip of the sheath is adjacent the outer vessel wall. This can be determined by known visualization techniques. The staging chamber is then attached to the proximal end of the sheath and used to hydrate and advance the pledget to the distal end of the sheath. The pledget may be advanced through the sheath around or beside the guidewire. Alternatively, the guidewire may be removed before the pledget is conveyed into the sheath. A proximal vent, as described above, is preferably used to position the pledget at the distal end of the sheath. The pledget is then delivered with the plunger.

A sheath 208 can also be used for delivery of the pledget 40 without first removing the sheath from the vessel, as shown in the embodiments in FIGS. 37 and 38. In this way, the sheath 208 maintains hemostasis at the vessel puncture site 210 while the distal end of the pledget 40 is positioned at a depth corresponding to the outer surface of the vessel wall 212.

As shown in FIG. 37, the pledget 40 can be placed directly into the sheath 208 such as by use of an introducer or staging chamber. Preferably, a proximal vent 214 is provided in the sheath 208 to position the pledget at a proper position within the sheath. The pledget 40 is delivered to the sheath and the proximal end of the pledget is positioned at a depth corresponding to the outer wall of the vessel 212. The proper positioning of the sheath and the pledget is achieved by locating an imaging marker 216 on the sheath at an outer wall of the vessel 212. The pusher 14 is then used to hold the pledget 40 stationary with respect to the vessel while the sheath 208 is withdrawn from the puncture site 210.

FIG. 38 illustrates an alternative embodiment of a sheath delivery system in which an introducer 12 is used to deliver a pledget 40 into the sheath 208. As in the embodiment of FIG. 37, the sheath 208 is maintained in the puncture site 210 during delivery of the pledget into the sheath. The introducer 12 may be inserted into the sheath 208 and secured to the sheath in a known manner such that the distal end of the pledget 40 is positioned at a depth corresponding to the outer surface of the vessel wall 212. The proper positioning may be determined by imaging a marker on the sheath 208 that corresponds to the distal end of the introducer 12. Alternatively, positioning can be determined by imaging either the introducer 12 or the pledget 40 if these elements are formed of an imaginable material. The plunger 14 is then used to hold the pledget 40 in position with respect to the vessel wall 212 while the sheath 208 and introducer 12 are withdrawn from the puncture site.

According to the embodiments of FIGS. 37 and 38, the sheath 208 maintains hemostasis of the puncture site 210 until a distal tip of the sheath has exited the puncture site. When the sheath exits the puncture site, the pledget 40 is exposed and begins to provide hemostasis. When the entire sheath 208 has been withdrawn the pledget is left within the tissue tract and provides continued hemostasis.

FIG. 11 illustrates a cross section of a distal end of an introducer 12b according to an alternative embodiment of the invention in which a central lumen 70 is provided within the introducer for receiving the guidewire 26. The central lumen 70 allows the guidewire to be inserted easily through the pledget 40. According to this embodiment the central lumen 70 is formed by a tube 72 which preferably extends at least the length of the hydrated pledget 40 when the pledget is positioned within the delivery chamber 36b. The tube 72 is supported by one or more ribs 74 connected to the exterior of the tube and to the interior wall of the introducer 12b. The pledget 40 for use with this embodiment is either formed with a generally U-shaped cross section to be accommodated in the U-shaped cross section of the delivery chamber 36b or deforms during loading to surround the one or more ribs 74 and tube 72.

FIG. 12 shows a proximal end of an introducer 12 connected to a specially designed connector 80 for connecting the introducer to the syringe 50. The connector 80 is used when the proximal end of the introducer 12 is larger in diameter than the standard syringe fitting. The connector 80 includes a first end 82 for connection to the syringe 50 and a second end 84 for connection to the introducer 12. In use, the connector 80 is removed from the introducer 12. The pledget 40 is then inserted into the introducer 12 and the connector 80 is reattached. The syringe 50 is then connected to the connector 80 for injection of fluid into the introducer 12 to hydrate, advance, and compress the pledget 40.

FIGS. 13–20 illustrate three different embodiments of templates for use in cutting a piece of a desired size from a sheet of sponge to form the pledget 40. FIG. 13 illustrates a template 108 having a rectangular shaped recess 110 with edges of the recess forming edge guides 112, 114. As shown in FIG. 15, the edge guides 112, 114 of the recess 110 are placed against the edges of a sheet 116 of sponge material. The template 108 is pressed downward and the sponge sheet is cut along two edges 118, 120 of the template 108.

An alternative embodiment of a template 124 is illustrated in FIG. 16–18. The template 124 includes a recess 126 with a single edge guide 127 and two pressure rails 128. The pressure rails 128 help to securely hold the template 124 on the sponge sheet 116 during cutting along cutting edges 130, 132 of the template. Although the templates of FIGS. 13 and 16 are illustrated with two cutting edges, it should be understood that the templates according to the present invention may include one or more cutting edges depending on the size and shape of the sheet 116 from which the piece of sponge material is to be cut. In addition, the templates may be provided with up to three edge guides 112, 114, 127. The templates are provided with recesses for ease of alignment of the templates with the sheet of sponge material. However, alignment may alternatively be provided by use of transparent templates with edge markings or by alignment with the edges of the template themselves. For example, the template may be formed of the same size as the sponge piece to be cut without any recess or edge guides.

FIGS. 19 and 20 show an alternative embodiment of a template 136 having a recess 138 and creasing ridges 140. The creasing ridges or ribs 140 will create creases in the sponge material to assist in folding or rolling of the pledget 40. Any number of creasing ridges 140 may be used depending on the configuration of the pledget to be formed. For example, creasing ridges 140 may be formed at evenly spaced intervals across the entire template surface. The creasing ridges 140 are preferably about 0.2 to 1.5 mm wide and about 0.5 to 2 mm high with a spacing of about 0.5 to 5 mm. The creasing ridges 140 also help to prevent movement between the template 136 and the sponge sheet 116 during cutting.

The templates 108, 124, 136 may be separate members included in a puncture closure kit including the introducer and pusher or may be fixed to one of the members of the puncture closure system. For example, the template may be attached to a staging chamber of the introducer 12.

FIGS. 21 through 24 illustrate vent caps for assisting in hydrating and staging pledgets within the delivery devices of the present invention. The vent caps provide the ability to more rapidly hydrate the pledget and provide the ability to locate the pledget at a desired axial location within the delivery device.

One preferred embodiment of a vent cap 144 for use on the distal end of the introducer 12 is shown in FIG. 21. The vent cap 144 is received over the distal end of the introducer 12, as shown in FIG. 22, with a rim 146 of the cap forming a friction fit with an exterior surface of the introducer. The vent cap 144 includes an interior dome 148 having a vent hole 150. Although the vent hole 150 has been illustrated in a center of the dome 148, the vent hole may be located at other positions or may be provided between the vent cap 144 and the distal end of the introducer 12. The vent hole 150 allows the operator to apply high pressures with the syringe to the interior of the introducer 12 and allows air and fluid to exit through the vent hole. This high pressure can be used to drive the pledget 40 to the distal end of the introducer and to drive fluid into the pledget causing very rapid hydration of the pledget material. High pressure is intended to mean pressures of about 5 psi or greater. The interior dome 148 allows a distal end of the pledget 40 to be positioned just distal of the distal end of the introducer 12. The vent cap 144 can be removed and the introducer 12 is then inserted over the proximal end of the guidewire and advanced to the puncture site. The pledget material extending from the distal end of the introducer 12 provides a rounded surface for assisting in passing the introducer through the layers of tissue to the blood vessel puncture site.

The shape of the interior dome 148 of the vent cap 144 may be modified to achieve different positions of the distal end of the pledget with respect to the distal end of the introducer 12. For example, if the pledget is to be contained completely within the introducer 12, an inverted dome, cone, or cylinder shaped vent cap may be used in which the dome, cone, or cylinder extends partially into the distal lumen of the introducer 12. Alternatively, if the pledget is to be positioned at the distal end of the introducer 12, the interior of the vent cap may be flat.

FIG. 23 illustrates an alternative embodiment of a vent cap 156 which is particularly configured for use with the separate staging chamber 170 of the introducer shown in FIG. 29. The vent cap 156 preferably includes a luer fitting 158 which is attachable to a distal end of the staging chamber 170. The vent cap 156 includes a finger 160 which extends to or into a distal end of the staging chamber 170. The finger 160 has a central vent 162. The use of the vent cap 156 with the finger 160 allows the pledget 40 to be held within the large diameter portion of the staging chamber 170 for quick and easy hydration of the pledget. The vent finger 160 functions to hold the pledget 40 within the large diameter portion of the staging chamber 170 while injection of fluid by the syringe is utilized to begin to hydrate the pledget and remove air from the staging chamber. The partially hydrated pledget moves forward to block the vent 162. If the vent 162 has not been entirely blocked by the pledget, the venturi effect will help draw the pledget toward the vent. Once the vent 162 is blocked, high pressure can be used to drive fluid into the pledget, causing very rapid hydration or super hydration of the pledget material. Although the vent 162 has been illustrated in the center of the finger 160, the vent may be located at other positions or may be provided between the vent cap 156 and the staging chamber 170.

For a delivery system employing the introducer 12 as illustrated in FIG. 1, a vent cap similar to that illustrated in FIG. 23 with an elongated finger 160 may be used. The elongated finger extends all the way to the staging chamber 34 to hold the pledget 40 within the staging chamber during hydration. After hydration of the pledget 40 within the staging chamber 34, the vent cap with the elongated vent finger is removed and the pledget is advanced into the delivery chamber.

According to an alternative embodiment, a cap without a vent can be used for hydration. The ventless cap acts as a plug to allow hydration by forcing fluid into the introducer which is oriented in a downward direction. Air displaced from the pledget and introducer escapes upward into the syringe during hydration. In addition, two of the vent caps can be connected in a single member when used with the same system.

FIG. 25 illustrates an alternative embodiment of a pusher 164 having a proximal stop 166 and a sliding luer 168 or other sliding fitting. The proximal stop 166 is provided proximal to an enlarged diameter distal portion 172 of the pusher 164. The sliding luer 168 is provided with an axial through hole having a diameter which is greater than a diameter of a proximal shaft 174 of the pusher 164 and smaller than the diameter of the proximal stop 166. The sliding luer 168 or other sliding fitting is configured to be attached to a proximal end of the introducer 12 or of a delivery chamber portion of a two part introducer. Once the sliding luer 168 has been attached to the introducer, the proximal movement of the pusher shaft 174 relative to the introducer is limited by the proximal stop 166 abutting the distal face of the sliding luer 168. This configuration of the pusher 164 is illustrated most clearly in FIG. 27 in which the pusher is illustrated as it is used with the introducer 12. The pusher 164 is illustrated in FIG. 27 prior to connection of the sliding luer 168 to the mating luer 42 on the introducer 12. When the mating luer 42 is locked to the sliding luer 168, the pledget 40 is confined between the distal end of the pusher 164 and the vent cap 144 which has been used to stage the pledget. Once the vent cap 144 is removed, the system is ready for delivery of the pledget 40 by advancing the system including the introducer 12 and the pusher 164 over a guidewire to the target site. Because the proximal movement of the pusher 164 is preset by the proximal stop 166, the pledget 40 cannot be displaced proximally during advancement over the guidewire. The pusher 164 also includes a proximal luer 176 which can be attached to the sliding luer 168 after delivery of the pledget 40. The introducer and pusher system can then be used to apply pressure to the pledget for local compression until hemostasis is achieved.

The proximal stop 166 has been described as formed by an enlarged diameter portion of the pusher 164. However, the proximal stop may also be provided by a disk or other protruding member on the pusher shaft or by a detent and corresponding projection.

According to an alternative embodiment of the invention, the functions of the sliding luer 168 and proximal stop 166 can be achieved with other features. For example, one or more detents, reliefs, or ratchet teeth provided on the pusher shaft may engage corresponding features on the introducer to locate the pusher at a desired position and prevent proximal movement of the pusher. FIGS. 28*a–f* illustrate examples of these systems.

FIGS. 28*a* and 28*b* illustrate an alternative embodiment of an adjustable proximal stop employing a ratchet mechanism. As shown in FIG. 28*a*, the introducer 12 includes one or more tabs 210 which engage ratchet teeth 212 on the pusher 14 to limit proximal motion of the pusher after insertion. This system improves deployment control by allowing the pusher position to be maintained at any point during deployment. The ratchet teeth 212 extend along at least a portion of the shaft of the pusher 14. One or more ratchet tabs 210 interact with the teeth 212 of the pusher, as shown most clearly in FIG. 28*b*.

FIG. 28*a* illustrates the use of the ratchet system to position the pusher 14 adjacent the proximal end of the pledget 40 and trap the pledget between the pusher and the vent cap 144 in preparation for use. Thus, the ratchet teeth 212 allow the system to accommodate pledgets 40 of varying sizes. The ratchet system can also provide for partial deployment of the pledget 40 while continuing to provide resistance to proximal motion of the pusher 14. This can be beneficial for example, for guidewire removal and/or system advancement with the pledget 40 in a partially deployed state.

Although the ratchet tabs 210 have been illustrated on the introducer 12 and the ratchet teeth 212 have been illustrated on the pusher 14, these elements may also be reversed. The ratchet teeth and tabs may also be provided on other portions of the system that interact, such as handles, luers, locks, or the sliding luer illustrated in FIG. 25.

FIGS. 28*c–f* illustrate systems having other features for resistance to axial sliding of the pusher 14. As shown in FIG. 28*c*, the introducer 12 is provided with one or more detents 214. The constant diameter pusher 14*d* of FIG. 28*d* is engaged by the detent 214 and provides a friction fit.

FIGS. 28*e* and 28*f* show alternative embodiments of pushers 14*e*, 14*f* having features which snap over the detent 214. These features include the grooves 216 and the proximal stop 218. The detent 214 can advantageously provide tactile feedback of pusher location to the user. As with the embodiment of FIG. 28*a* employing ratchet teeth and tabs, the detent 214 and corresponding features may be located on different parts of the system.

FIG. 26 illustrates one preferred embodiment of the distal end of the pusher 164 having an interior funnel 178 for ease in loading the pusher over a guidewire. As a proximal end of the guidewire is advanced into the pusher 164, the distal funnel 178 guides the guidewire smoothly into the lumen of the pusher. The distal funnel 178 provides a particular advantage for facilitating blind loading of the pusher 164 over a guidewire when the pusher is already positioned within the introducer 12 or another delivery system.

Although the relative motion of the pusher 14 and the introducer 12 has been described as provided manually, this motion may also be provided by an automatic or spring loaded actuation mechanism.

FIGS. 29–32 illustrate one preferred delivery system according the present invention in which the introducer is a two part introducer including a separate staging chamber 170 and a delivery chamber 180. The entire delivery system of FIG. 29 preferably includes the staging chamber 170, the delivery chamber 180, the pusher 164, and one or more vent caps for the staging and/or delivery chambers such as those illustrated in FIGS. 21 and 23. According to this embodiment, the staging chamber 170 is used with the vent cap 156 of FIG. 23 and a syringe for hydration of the pledget 40 within the staging chamber. The vent cap 156 is then removed from the staging chamber 170 and the staging chamber is connected to the delivery chamber as illustrated in FIG. 30. The pledget 40 is advanced from the staging chamber 170 to the delivery chamber 180 by attaching a syringe to a luer fitting 184 at the proximal end of the staging chamber and providing the vent cap 144 on the distal end of the delivery chamber 180. With this assembly, the hydrated pledget is advanced to the distal end of the delivery chamber 180. The staging chamber 170 is then removed from the delivery chamber 180 in preparation for pledget delivery.

As shown in FIG. 31, the pusher 164 is inserted into the delivery chamber 180, the sliding luer 168 is fixed to a distal luer 186 of the delivery chamber, and the vent cap 144 is removed. This system is used as previously described to deliver the pledget 40 over a guidewire to a delivery site.

FIG. 32 illustrates the delivery system of FIG. 31 after the pledget 40 has been delivered by relative movement between the pusher 164 and the delivery chamber 180. As shown in FIG. 32, the proximal luer 176 of the pusher 164 is engaged with the sliding luer 168 and the system may be used to apply pressure in the direction of the arrow P to provide local compression and promote hemostasis. The delivery system employing separate staging and delivery chambers 170, 180 provides the advantage of a shorter delivery system which can be handled more easily and used with shorter guidewires.

The two component introducer system also allows components to be mixed and matched. For example, one staging chamber 170 maybe used with multiple delivery chambers 180 of different sizes. In addition, the staging and delivery chambers can be formed of different materials for their different material properties. For example, it may be desirable to have a transparent plastic staging chamber 170 so that the user can view the pledget within the staging chamber and determine when the pledget has been completely hydrated. It may also be desirable to have a delivery chamber 180 formed of stainless steel or other opaque material which is strong, relatively thin, and less expensive to manufacture. FIGS. 33 and 34 illustrate alternative embodiments of dilators having distal ends with dilator strain relief features. Conventional dilators have distal ends with relatively blunt or spherical shapes and having dilator lumens which extend through the length of the dilator and are sized to accomodate a guidewire. When these dilators are advanced into an access tract, the leading blunt or rounded edge of the dilator often encounters tissue layers within the subtutaneous tissue that require substantial force to advance the dilator through these layers. A difficult tissue layer may yield both axially and laterally under the load applied by the dilator. Lateral movement of the dilator can cause significant deflection of the guidewire and often results in a kinked guidewire. This increases the challenge of properly introducing the dilator into the tissue tract.

FIG. 33 illustrates a dilator 190 having a flexible distal extension 192 with a diameter which is much smaller than an outer diameter of the dilator. For example, the dilator 190 may have a diameter of about 3 to 5 mm while the extension 192 has a diameter of about 1 to 2 mm. The small diameter flexible distal extension 192 helps to guide the guidewire into the dilator 190 and reduces the stress concentration on the guidewire when difficult tissue layers are encountered.

Another alternative embodiment of a dilator 196 is illustrated in FIG. 34 in which a funnel shaped lumen 198 at a distal end of the dilator provides a guidewire strain relief feature. The enlarged distal opening 200 of the dilator 196 allows some guidewire deflection to occur without kinking the guidewire as the dilator is advanced over the guidewire. The funnel shaped lumen 198 also allows easier passage of kinked guidewires.

Among other advantages, the absorbable sponge delivery system according to the present invention permits the delivery of more absorbable sponge material down a smaller tract by hydrating and compressing the absorbable sponge material. The over the wire delivery method ensures that the absorbable sponge pledget 40 is delivered directly over the puncture site and remains in the proper position while hemostasis is achieved. The vessel depth indicator system ensures that the absorbable sponge material is positioned adjacent the exterior of the blood vessel and does not extend into the blood vessel to possibly induce thrombosis. The kneading of the absorbable sponge material during rolling of the dry sponge and while hydrated and passing through the introducer improves the expansion properties of the sponge material.

The absorbable sponge material can be absorbed by the body in a period of time between several days and several months depending on the absorbable sponge material used. A pledget 40 formed of commercially available Gelfoam material will be absorbed by the body within 1 to 6 weeks. However, the pledget material may be engineered to provide different rates of absorption. For example, Gelfoam can be designed to be absorbed at different rates by varying the degree of cross-linking. Preferably, the pledget 40 is designed to be absorbed in less than one month.

Although the invention is primarily intended for delivery of absorbable sponge, non-absorbable sponge may also be delivered with the devices, systems, and methods of the present invention. A non-absorbable sponge may be desirable where it will be necessary to locate the blood vessel puncture after the procedure.

Although the pledget 40 has been described as formed from a rectangular shaped piece of an absorbable sponge material which is rolled into a cylindrical shape, the pledget may also be formed in different shapes and rolled from different shaped sheets. For example, the pledget 40 may be preformed in a variety of cross sections including circular, rectangular, star, or other multi-sided shape. The pledget 40 may have a folded cross section and may have through or blind holes formed in the dry pledget. In addition, the pledget size and shape can be matched to the size and shape of a particular delivery site.

While an amorphous or discontinuous sponge structure may be used in the present invention, a continuous structure of the delivered absorbable sponge pledget 40 provides more secure and reliable placement of a plug of material against the blood vessel puncture than a paste or liquid. The continuous sponge structure can even facilitate partial withdrawal, removal, or movement of the ejected pledget.

In accordance with one aspect of the invention, the absorbable sponge material can be hydrated with a clotting agent such as thrombin, a contrast agent, another beneficial agent, a combination of agents, or the like. Alternatively, the pledget material itself may contain an agent such as a clotting agent, a contrast agent, another beneficial agent, a combination of agents, or the like.

The absorbable sponge pledget 40 may be presoaked with a beneficial agent such as thrombin for delivery of the beneficial agent to the punctured blood vessel. Alternatively, the pledget 40 may be hydrated with a beneficial liquid agent used as the hydrating fluid within the syringe 50. Further, the beneficial agent may be delivered to the pledget 40 after the pledget is ejected at the blood vessel puncture site through the lumen of the pusher 14 or through the introducer 12.

The treatment of a blood vessel puncture with a hydrated and injected pledget 40 of absorbable sponge to facilitate hemostasis provides substantial advantages in comfort over external pressure methods. In addition, the present invention also provides advantages over the insertion of an absorbable sponge material in a dry state or injection of a liquid or paste. In particular, the hydration and manipulation or "kneading" of the hydrated Gelfoam pledget 40 as it is passed through the introducer 12 improves the expansion and absorption characteristics of the Gelfoam. The injected Gelfoam conforms in shape quickly to the shape of the puncture site and immediately begins blocking blood flow through the puncture site and providing local compression. In contrast, a dry piece of sponge material does not swell until the blood has sufficiently saturated the sponge material, which can take up to hours. The hydrated and kneaded sponge material will expand to a larger size much more quickly when wetted than a piece of dry sponge material when wetted.

Because the amount of subcutaneous fat and tissue between the skin 106 and the blood vessel 102 varies between patients from approximately 0.5 cm to 15 cm or more the system may be provided in different lengths for use in different patients. The pledget 40 size and shape may also be varied for different patients. The absorbable sponge material should form a complete plug over the puncture site without expanding into the blood vessel or exiting the skin of the patient. In some instances where the amount of subcutaneous tissue is great it may be desirable to deliver multiple pledgets 40 in spaced apart positions along the tract leading to the puncture site.

The particular size and shape of the introducer 12 may vary depending on the size of the access site, amount of subcutaneous tissue, and the size of pledget 40 to be delivered. According to one example of the present invention, a pledget 40 is formed from a rectangular piece of pre-compressed Gelfoam approximately 2 by 3 cm with a thickness of 0.15 cm. The Gelfoam is rolled or folded into a pledget having a length of approximately 3 cm. An introducer 12 for delivery of this pledget to a patient with an average amount of subcutaneous tissue has a staging chamber length of about 2.5 to 6 cm, preferably approximately 3 cm, a staging chamber inner diameter of about 0.12 to 1.5 cm, preferably approximately 0.4 cm, and a delivery chamber 36 which is typically longer than the staging chamber and has an inner diameter smaller than that of the staging chamber of about 1 cm or less, preferably approximately 0.33 cm or less. The particular length of the delivery chamber 36 depends on both the subcutaneous tissue depth of the patient and the linear expansion of the pledget 40 as it moves from the staging chamber 34 to the delivery chamber. An angle made by a wall of the tapered section 38 with a longitudinal axis of the adaptor 12 may vary from about 5° to 90°, but is preferably between about 30° and 60°, more preferably approximately 45°. The tapered section 38 is illustrated with a substantially planar interior surface, when shown in cross section. However, the tapered section 38 may also have a convex or concave surface in cross-section. This example of pledget 40 and introducer 12 configurations is merely exemplary of the present invention.

In accordance with an alternative embodiment of the invention, the pledget 40 may be provided with a rapidly dissolvable tip extending from a distal end of the pledget. Examples of rapidly absorbable or dissolvable tip materials include water-soluble, biocompatible, non-toxic, and preferably non-immunogenic polymers such as poly vinyl alcohol (PVA) and ploy vinyl pyrrolidone (PVP). Other examples could include gelatin derived from porcine or bovine sources. Still other possible tip materials could include, but are not limited to, poly lactic-glycolic acid, poly(proline), ploy(ethylene oxide) and carbowaxes, methyl cellulose, carboxymethyl cellulose, poly(acrylic acid), poly (hydroxyethyl methacrylate), poly(acrylamide), natural plant gums, and poly(methyl vinyl ether-maleic anhydride).

FIGS. 35 and 36 illustrate a pledget 40a with a rapidly dissolvable tip 200. The rapidly dissolvable tip 200 is arranged to extend slightly into the blood vessel 102 and will provide an additional locating mechanism which will hold the pledget at the proper position over the puncture after the guidewire is removed as shown in FIG. 36. Preferably, the tip 200 extends from the end of the pledget a length not shorter than one wall thickness of the target vessel and not exceeding one wall thickness plus the lumen diameter of the target vessel. Dissolution rates are preferably sufficient to facilitate complete absorption of the rapidly dissolvable tip in the lumen within time periods as short as one minute and not exceeding 72 hours. Preferably, the pledget with the dissolvable tip can also be inserted without the use of the guidewire 26 and the dissolvable tip can serve the locating function of the guidewire for accurately positioning the pledget over the blood vessel puncture.

The rapidly dissolvable tip 200 may be formed from a thin walled tube which extends from an end of the pledget. For example, the thin walled tube may be rolled within the pledget. The guidewire may be threaded through the thin walled tube of the dissolvable locating tip or along one side the locating tip.

As an alternative to the dissolvable tip 200, the locating tip may be formed of a non-dissolvable material and may be removable. For example, the removable tip material may extend through the pledget and all the way to the skin surface. The tip may be withdrawn after a predetermined time when the locating function of the tip is no longer needed.

While the invention has been described in detail with reference to the preferred embodiments thereof, it will be apparent to one skilled in the art that various changes and modifications can be made and equivalents employed, without departing from the present invention.

What is claimed is:

1. A method of super hydrating an absorbable sponge material for delivery to a body for facilitating hemostasis, the method comprising:
   placing a dry piece of absorbable sponge in a delivery device; and
   subjecting the absorbable sponge to a fluid to rapidly and completely hydrate the absorbable sponge in the delivery device, wherein the fluid is at about 5 psi or greater.

2. The method according to claim 1, wherein the absorbable sponge is provided with a clotting agent.

3. The method according to claim 1, wherein the fluid used for hydrating the absorbable sponge includes a therapeutic agent.

4. The method according to claim 1, wherein the fluid used for hydrating the absorbable sponge includes a clotting agent.

5. The method according to claim 1, wherein the delivery device is tubular, and the dry piece of absorbable sponge in the delivery device is subjected to the fluid, and delivered from the tubular delivery device in a hydrated state.

6. The method according to claim 5, wherein the hydrated piece of absorbable sponge is delivered to the body by a pusher.

7. The method according to claim 1, wherein the fluid is injected into the delivery device.

8. The method according to claim 7, wherein the fluid is injected into the delivery device by connecting a syringe to a first end of the delivery device.

9. The method according to claim 8, wherein a vent cap is placed on a second end of the delivery device while the fluid is injected into the delivery device.

10. A method of super hydrating an absorbable sponge material for delivery to a body, the method comprising subjecting the absorbable sponge to a fluid to hydrate the absorbable sponge, wherein the fluid is at about 5 psi or greater.

11. The method according to claim 10, wherein the absorbable sponge is placed in a delivery device and the fluid is injected into the delivery device.

12. The method according to claim 10, wherein the hydrated absorbable sponge is delivered to a body for facilitating hemostasis.

13. The method according to claim 10, further comprising a step of piercing the hydrated sponge with a delivery device.

14. A method of super hydrating an absorbable sponge material for delivery to a body, the method comprising:
   placing a dry piece of absorbable sponge in a delivery device; and
   subjecting the absorbable sponge to a fluid to rapidly and completely hydrate the absorbable sponge in the delivery device, wherein the fluid is at about 5 psi or greater.

15. The method according to claim 14, wherein the fluid is injected into the delivery device.

16. A method of super hydrating an absorbable sponge material for delivery to a body for facilitating hemostasis, the method comprising:
   placing a dry piece of absorbable sponge in a delivery device; and
   subjecting the absorbable sponge to a fluid to rapidly and completely hydrate the absorbable sponge wherein the delivery device is placed in a pressurized container of fluid.

17. A method of super hydrating an absorbable sponge material for delivery to a body for facilitating hemostasis, the method comprising:
   placing a dry piece of absorbable sponge in a delivery device; and
   subjecting the absorbable sponge to a fluid to rapidly and completely hydrate the absorbable sponge in the delivery device, wherein the dry piece of absorbable sponge is rolled up prior to placing the sponge in the delivery device.

18. A method of super hydrating an absorbable sponge material for delivery to a body for facilitating hemostasis, the method comprising:
   placing a dry piece of absorbable sponge in a delivery device; and
   subjecting the absorbable sponge to a fluid to rapidly and completely hydrate the absorbable sponge in the delivery device, wherein the delivery device has a tapered lumen.

19. A method of super hydrating an absorbable sponge material for delivery to a body for facilitating hemostasis, the method comprising:

placing a dry piece of absorbable sponge in a delivery device; and subjecting the absorbable sponge to a fluid to rapidly and completely hydrate the absorbable sponge in the delivery device, wherein the fluid used for hydrating the absorbable sponge is a sterile saline solution.

20. A method of super hydrating an absorbable sponge material for delivery to a body for facilitating hemostasis, the method comprising:

placing a dry piece of absorbable sponge in a delivery device; and subjecting the absorbable sponge to a fluid to rapidly and completely hydrate the absorbable sponge in the delivery device, wherein the absorbable sponge is provided with a contrast agent to facilitate visualization.

21. A method of super hydrating an absorbable sponge material for delivery to a body for facilitating hemostasis, the method comprising:

placing a dry piece of absorbable sponge in a delivery device; and subjecting the absorbable sponge to a fluid to rapidly and completely hydrate the absorbable sponge in the delivery device, wherein the fluid used for hydrating the absorbable sponge includes a contrast agent to facilitate visualization.

* * * * *